United States Patent [19]
Shibata et al.

[11] Patent Number: 5,756,759
[45] Date of Patent: May 26, 1998

[54] PYRAZOLE COMPOUNDS HAVING A THIOCHROMAN RING AND PESTICIDES CONTAINING SUCH COMPOUNDS

[75] Inventors: Mitsuru Shibata, Sodegaura; Ichiro Nasuno, Ichihara; Kazuyoshi Koike; Masashi Sakamoto, both of Sodegaura, all of Japan

[73] Assignee: Idemitsu Kosan Co., Ltd., Tokyo, Japan

[21] Appl. No.: 637,781

[22] PCT Filed: Nov. 8, 1994

[86] PCT No.: PCT/JP94/01881

§ 371 Date: Jun. 27, 1996

§ 102(e) Date: Jun. 27, 1996

[87] PCT Pub. No.: WO95/13275

PCT Pub. Date: May 18, 1995

[30] Foreign Application Priority Data

Nov. 9, 1993 [JP] Japan .................. 5-279211
May 17, 1994 [JP] Japan .................. 6-102528
May 27, 1994 [JP] Japan .................. 6-115338

[51] Int. Cl.$^6$ .............. A01N 43/56; A01N 43/50; C07D 409/06; C07D 335/06
[52] U.S. Cl. .................. 548/364.4; 504/282
[58] Field of Search .............. 548/364.4; 502/137; 504/282

[56] References Cited

U.S. PATENT DOCUMENTS 4,002,619  1/1977  Dengler et al. .......... 548/364.4 X
4,986,845  1/1991  Oya et al. .............. 540/140 X
5,468,722  11/1995 Shibata et al. ........... 504/282

FOREIGN PATENT DOCUMENTS 0129765   1/1985   European Pat. Off. .......... 548/364.4
63-122672 5/1988   Japan .
63-122673 5/1988   Japan .
63-170365 7/1988   Japan .
1-52759   2/1989   Japan .
2-288866  11/1990  Japan .
93-18031  9/1993   WIPO .................. 548/364.4

Primary Examiner—Floyd D. Higel
Attorney, Agent, or Firm—Frishauf, Holtz, Goodman, Langer & Chick, P.C.

[57] ABSTRACT

Pyrazole compounds of the formula (I)

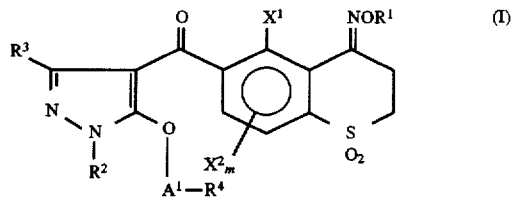

and the formula (XI),

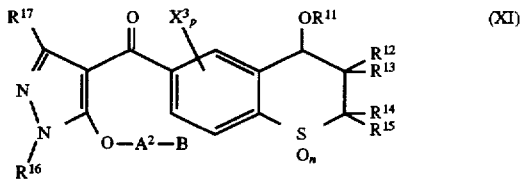

and the pyrazole compounds of the formula (I) exhibits selectivity to paddy rice and corn, and can control a wide range of paddy field and upland field weeds at a low dosage.

11 Claims, 5 Drawing Sheets

PYRAZOLE COMPOUNDS HAVING A THIOCHROMAN RING AND PESTICIDES CONTAINING SUCH COMPOUNDS

TECHNICAL FIELD

The present invention relates to a pyrazole derivative and a herbicide containing the same.

TECHNICAL BACKGROUND

Herbicides are very important chemicals for the labor-saving in weed control work and for increasing the productivity for agricultural and horticultural products. Herbicides have been therefore actively studied and developed for many years, and a variety of chemicals are practically used at present. Even today, however, it is desired to develop novel chemicals having distinguished herbicidal properties, particularly chemicals which are free of toxicity to cultured crops and can control target weeds selectively in a low dosage.

During a growing period of corn, etc., a triazine-based herbicide such as atrazine and acid anilide-based herbicides such as alachlor and metolachlor have been conventionally used. However, atrazine shows low efficacy to gramineous weeds, and alachlor and metolachlor show low efficacy to broad-leaved weeds. It is therefore difficult at present to control gramineous weeds and broad-leaved weeds together with a single herbicide. Further, the above herbicides are undesirable in view of an environmental problem due to their high dosage requirement.

Further, it is known that a paddy field grows not only paddy rice but also various weeds including annual gramineous weeds such as barnyard grass, annual cyperaceous weeds such as umbrella plant, annual broad-leaved weeds such as monochoria and toothcup and perennial weeds such as *Sagittaria pygmaea miquel*, largeleaf pondweed, oriental waterplantain, bulrush, needle-upright clubrush, *Cyperus serotinus rottboell*, water chestnut, arrowhead and dropwort. It is very important for rice cultivation to effectively control these weeds without causing phytotoxicity to paddy rice and by spraying a chemical in a small dosage in view of environmental pollution. It is known that chemicals having high herbicidal activity to barnyard grass are generally liable to cause phytotoxicity to paddy rice, and it is an especially essential object remaining to achieve to develop a chemical which exhibit high herbicidal activity to barnyard grass which is gramineous weed and has excellent intergenus selectivity between paddy rice and barnyard grass.

Meanwhile, it is already known that specific 4-benzoylpyrazole derivatives have herbicidal activity (see JP-A-63-122672, JP-A-63-122673, JP-A-63-170365, JP-A-1-52759, JP-A-2-173 and JP-A-2-288866).

Typical examples of the 4-benzoylpyrazole derivatives (A) and (B) described in the above publications ((A); Compound No. 35 in JP-A-2-173, (B); Compound No. 1 in JP-A-63-122672) are as follows.

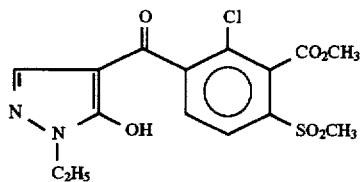

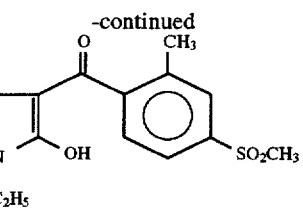

However, the 4-benzoylpyrazole derivatives which have been so far disclosed have herbicidal activity, but are insufficient in practical use. In particular, they are very inferior in herbicidal activity to gramineous weeds such as barnyard grass and green foxtail. Further, when used as a herbicide in a paddy field, the above chemicals may cause phytotoxicity to paddy rice since they have poor selectivity between paddy rice and gramineous weeds.

The present inventors have therefore proposed pyrazole derivatives having a thiochroman ring by already applying a patent (see PCT/JP93/00274; WO93/18031). Typical example C (Compound No. 66) of compounds described in the specification of the above patent application is as follows.

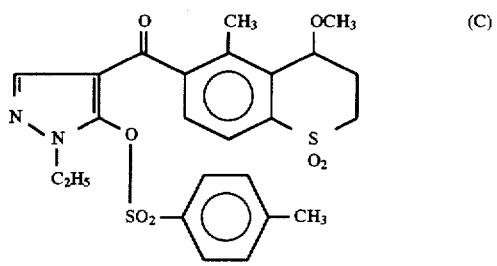

However, the above compound has high herbicidal activity to paddy rice, while its safety to paddy rice is not fully satisfactory.

The present invention has been made in view of the above circumstances, and the object thereof is to provide a pyrazole derivative which is free of phytotoxicity to corn and paddy rice and can control a wide range of upland weeds and paddy field weeds, particularly barnyard grass in a paddy field, in a low dosage, and a herbicide containing the pyrazole derivative.

DISCLOSURE OF THE INVENTION

The present inventors have made diligent studies to achieve the above object, and have found that a novel compound of the following general formula (I) shows selectivity to corn and paddy rice and can control a wide range of upland field and paddy field weeds in a low dosage, whereby the present invention has been completed.

Further, the present inventors have found that a pyrazole derivative of the following general formula (XI) is free of phytotoxicity to paddy rice and can control a wide range of upland field weeds and paddy field weeds, particularly barnyard grass and umbrella plant in a paddy field, in a low dosage, and have arrived at the completion of the present invention.

Therefore, the gist of the present invention consists in a pyrazole derivative of the general formula (I),

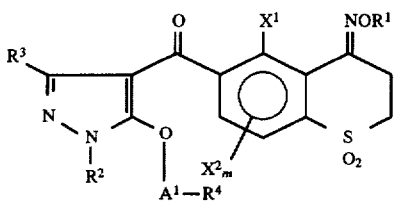

and a pyrazole derivative of the general formula (XI).

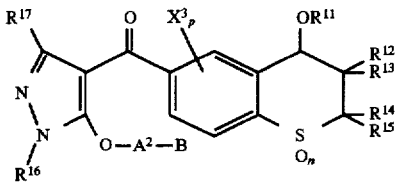

PREFERRED EMBODIMENTS FOR WORKING THE INVENTION

Figure 1:
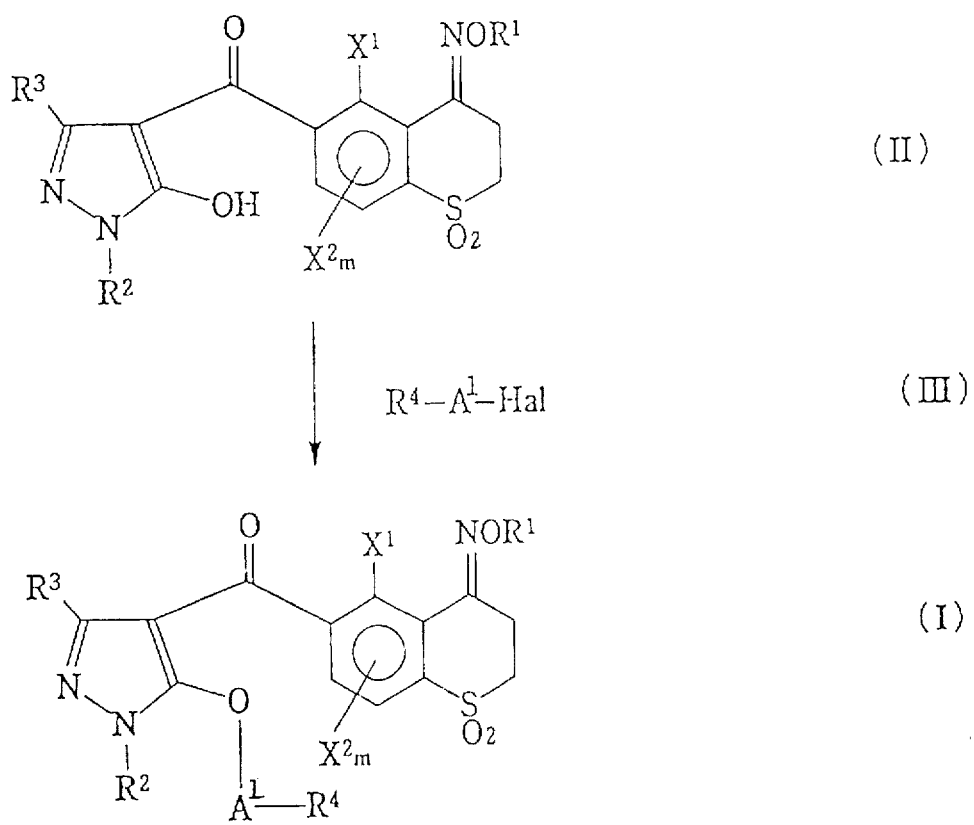
FIG. 1 shows the step of producing the pyrazole derivative of the formula (I) provided by the present invention.

The pyrazole derivative of the general formula (I) will be explained first.

In the general formula (I) for this pyrazole derivative, $R^1$ is a $C_1$–$C_6$ alkyl group such as methyl, ethyl, propyl, butyl, pentyl or hexyl. The propyl, butyl, pentyl and hexyl may be linear, cyclic or branched. $R^1$ is preferably a $C_1$–$C_4$ alkyl group, more preferably methyl or ethyl.

Each of $R^2$, $X^1$ and $X^2$ is independently a $C_1$–$C_4$ alkyl group. The $C_1$–$C_4$ alkyl group includes methyl, ethyl, propyl and butyl, and the propyl and butyl may be linear, cyclic or branched. $R^2$, $X^1$ and $X^2$ are preferably methyl or ethyl.

$R^3$ is hydrogen or a $C_1$–$C_4$ alkyl group. The $C_1$–$C_4$ alkyl group includes those described concerning the above $R^2$, $X^1$ and $X^2$. $R^3$ is preferably hydrogen or methyl, more preferably hydrogen. The propyl and butyl may be linear or branched.

m shows the number of $X^2$ and is 0 or 1. When m is 1, the position on which $X^2$ is substituted is preferably the 8-position.

$R^4$ is a $C_1$–$C_{10}$ alkyl group or a group of

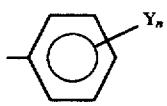

Specific examples of the $C_1$–$C_{10}$ alkyl group as $R^4$ include methyl, ethyl, propyl, butyl, pentyl, hexyl, heptyl, octyl, nonyl and decyl. The propyl, butyl, pentyl, hexyl, heptyl, octyl, nonyl and decyl may be linear, cyclic or branched. $R^4$ is preferably a $C_1$–$C_4$ alkyl group.

In the group of

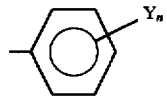

as $R^4$, Y is a halogen atom, nitro, a $C_1$–$C_4$ alkoxy group or a $C_1$–$C_4$ alkyl group. The halogen atom includes fluorine, chlorine, bromine and iodine. The $C_1$–$C_4$ alkyl group includes those described concerning the above $R^2$. Y is preferably chlorine, fluorine, nitro, methyl or methoxy.

n shows the number of Y and is 0 or an integer of 1 to 3. $A^1$ is

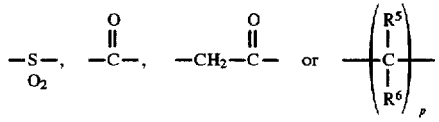

in which each of $R^5$ and $R^6$ is independently hydrogen or a $C_1$–$C_4$ alkyl group and p is 0 or an integer of 1 to 4. The $C_1$–$C_4$ alkyl group as $R^5$ and $R^6$ includes those described concerning the above $R^2$, $X^1$ and $X^2$.

Further, the pyrazole derivative of the formula (I) includes geometrical isomers based on an alkoxyimino group as shown in the following formulae (Ia) and (Ib), and the pyrazole derivative of the present invention may be any one of these isomers and a mixture of these. When m=1, the substituent $X^2$ can bond to the 7-position or the 8-position, while it preferably bonds to the 8-position.

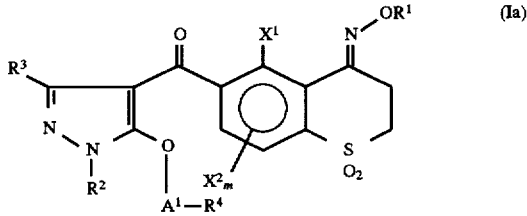

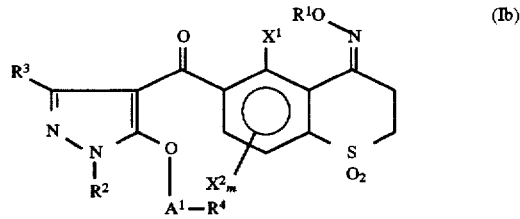

The pyrazole derivative of the general formula (XI) will be explained hereinafter.

In the formula (XI) for this pyrazole derivative, $R^{11}$ is a $C_1$–$C_6$ alkyl group such as methyl, ethyl, propyl, butyl, pentyl or hexyl, and the propyl, butyl, pentyl and hexyl may be linear or branched. $R^{11}$ is preferably a $C_1$–$C_4$ alkyl group, more preferably methyl, ethyl or i-propyl.

Each of $R^{12}$, $R^{13}$, $R^{14}$ and $R^{15}$ is independently hydrogen or a $C_1$–$C_4$ alkyl group. The $C_1$–$C_4$ alkyl group includes methyl, ethyl, propyl and butyl, and the propyl and butyl may be linear or branched. $R^{12}$, $R^{13}$, $R^{14}$ and $R^{15}$ are preferably hydrogen or methyl, more preferably hydrogen.

$R^{16}$ is a $C_1$–$C_4$ alkyl group, and specific examples thereof include those described concerning the above $R^{12}$ to $R^{15}$. $R^{16}$ is preferably methyl or ethyl.

$R^{17}$ is hydrogen or a $C_1$–$C_4$ alkyl group, and the $C_1$–$C_4$ alkyl group includes those described concerning the above $R^{12}$ to $R^{16}$. $R^{17}$ is preferably hydrogen or methyl.

$X^3$ is a $C_1$–$C_4$ alkyl group or a halogen atom. The former $C_1$–$C_4$ alkyl group includes those described concerning the above $R^{12}$ to $R^{16}$. The latter halogen atom includes chlorine, bromine, iodine and fluorine. $X^3$ is preferably a $C_1$–$C_4$ alkyl group, more preferably methyl.

p shows the number of $X^3$, and is an integer of 0, 1 or 2. When p is 2, one of a plurality of $X^3$s may be the same as, or different from, the other. p is preferably 1 or 2, the substitution portion is preferably the 5-position, or the substitution portions are preferably the 5-position and the 8-position.

n shows the number of oxygen atoms bonding to sulfur atom, and is an integer of 0, 1 or 2. When n=0, a sulfide is represented. When n=1, a sulfoxide is represented. When n=2, a sulfone is represented. Preferred is n=2 (sulfone).

$A^2$ is at least one selected from

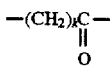

and —$CR^{18}R^{19}$.

In the above formulae for $A^2$, each of $R^{18}$ and $R^{19}$ is independently hydrogen or a $C_1$–$C_4$ alkyl group, and the $C_1$–$C_4$ alkyl group includes those described concerning the above $R^{12}$ to $R^{16}$. $R^{18}$ and $R^{19}$ are preferably hydrogen.

Further, in $A_2$, k shows the number of methylene chains and is an integer of 0 to 3, preferably 0 or 1. When k=0, it means that no methylene chain exists and that $A^2$ is carbonyl.

B is one selected from a $C_1$–$C_{12}$ alkyl group, a cycloalkyl group and a group of

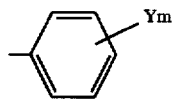

In the formula for B, Y is hydrogen, a $C_1$–$C_4$ alkyl group, a $C_1$–$C_4$ alkoxy group, a $C_1$–$C_4$ haloalkyl group, nitro or a halogen atom, and m shows the number of Y and is an integer of 1 or 2.

When $A^2$ is

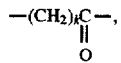

k is preferably 0 or 1, and B is a $C_1$–$C_4$, alkyl group, a cycloalkyl group or a halogen-substituted or halogen-nonsubstituted phenyl group.

When $A^2$ is —$CR^{18}R^{19}$, $R^{18}$ and $R^{19}$ are preferably hydrogen, and B is a phenyl group. The pyrazole derivative of the general formula (XI) contains asymmetric carbons, and includes a variety of isomers, while the pyrazole derivative of the present invention includes all the isomers and a mixture of the isomers.

The herbicide of the present invention contains, as an active ingredient, at least one selected from the novel pyrazole derivative of the formula (I) provided by the present invention and the novel pyrazole derivative of the formula (XI) provided by the present invention. These compounds are used by mixing them with a liquid carrier such as a solvent or a solid carrier such as a mineral fine powder and preparing the resultant mixtures in the form of a wettable powder, an emulsifiable concentrate, a dust or granules. For imparting these compounds with emulsifiability, dispersibility or spreadability when the above preparations are formed, a surfactant may be added.

When the herbicide of the present invention is used in the form of a wettable powder, generally, 10 to 55% by weight of the pyrazole derivative of the present invention, 40 to 88% by weight of a solid carrier and 2 to 5% by weight of a surfactant are mixed to prepare a composition, and the composition can be used.

When the herbicide of the present invention is used in the form of an emulsifiable concentrate, generally, the emulsifiable concentrate can be prepared by mixing 20 to 50% by weight of the pyrazole derivative of the present invention, 35 to 75% by weight of a solvent and 5 to 15% by weight of a surfactant.

When the herbicide of the present invention is used in the form of a dust, generally, the dust can be prepared by mixing 1 to 15% by weight of the pyrazole derivative of the present invention, 80 to 97% by weight of a solid carrier and 2 to 5% by weight of a surfactant.

Further, when the herbicide of the present invention is used in the form of granules, the granules can be prepared by mixing 1 to 15% by weight of the pyrazole derivative of the present invention, 90 to 97% by weight of a sold carrier and 2 to 5% by weight of a surfactant.

The above solid carrier is selected from mineral powders, and examples of the mineral powders include oxides such as diatomaceous earth and slaked lime, phosphates such as apatite, sulfates such as gypsum and silicates such as talc, pyrophyllite, clay, kaolin, bentonite, acidic terra abla, white carbon, powdered quartz and powdered silica.

The solvent is selected from organic solvents, and specific examples of the solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

The surfactant is selected from anionic surfactants, nonionic surfactants, cationic surfactants and amphoteric surfactants (amino acid and betaine).

The herbicide of the present invention may contain, as an active ingredient, other herbicidally active component as required in addition to the pyrazole derivative of the general formula (I) and/or the pyrazole derivative of the general formula (XI). The "other" herbicidally active component includes conventionally known herbicides such as phenoxy-based, diphenyl ether-based, triazine-based, urea-based, carbamate-based, thiol carbamate-based, acid anilide-based, pyrazole-based, phosphoric acid-based, sulfonylurea-based and oxadiazone-based herbicides. The "other" herbicidally active component is properly selected from the above herbicides.

The herbicide of the present invention may be used as a mixture with a pesticide, a fungicide, a plant growth regulator, a fertilizer, etc.

The novel pyrazole derivative of the present invention can be produced by the method shown in FIG. 1 (in which $X^1$, $X^2$, $R^1$, $R^2$, R3, $R^4$, m, n, p, $A^1$, $R^5$ and $R^6$ represent those which are already defined, and Hal is a halogen atom).

In this method, the molar ratio of the reaction reagent of the formula (III) to the starting material of the formula (II) is preferably 1:1 to 1:3. For collecting hydrogen halide formed as a byproduct by the reaction, it is preferred to use a base such as sodium carbonate, potassium carbonate, triethylamine or pyridine in a molar amount equivalent to, or greater than, the amount of the starting material of the formula (II). The reaction temperature is preferably set at a temperature between room temperature and the boiling point of a solvent used. The solvent used for this reaction is selected from aromatic hydrocarbons such as benzene and toluene, ether solvents such as diethyl ether, and halogenated hydrocarbon solvents such as methylene chloride and chloroform.

Further, a two-phase solvent of the above solvent and water may be used. In this case, a favorable result can be obtained by adding a phase transfer catalyst such as crown ether or benzyl chloride triethylammonium to the reaction system.

Figure 2:
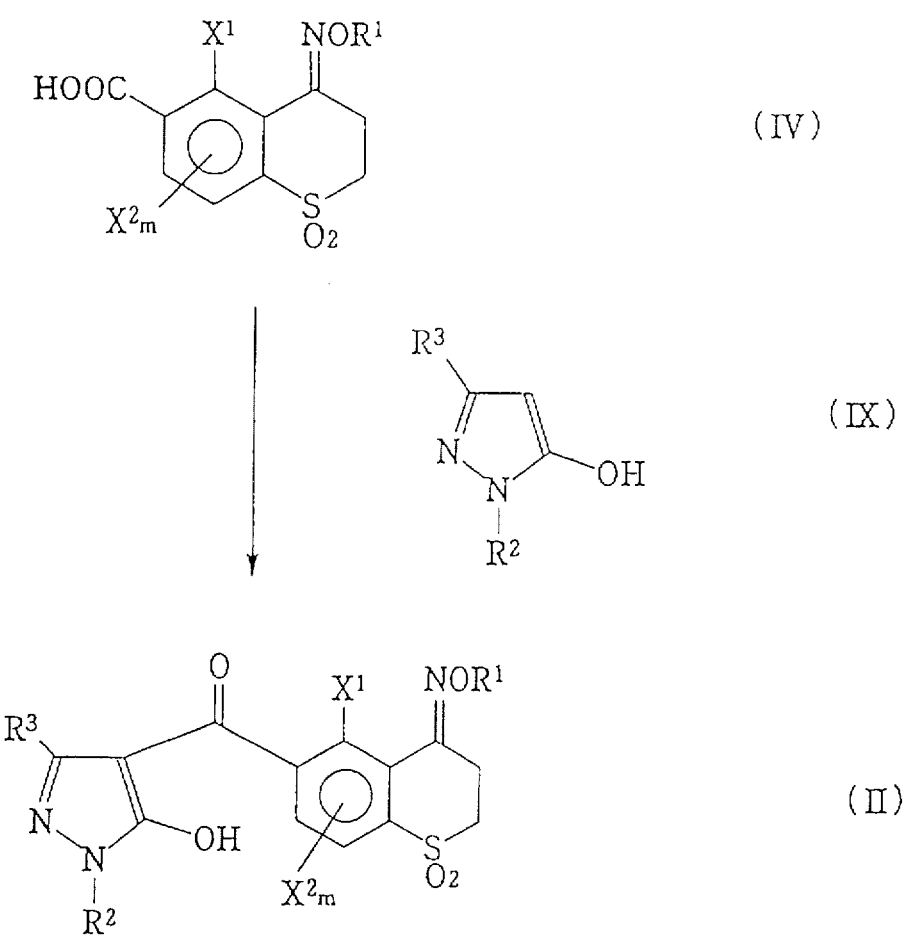
FIG. 2 shows the step of producing the compound of the general formula (II).

The compound of the formula (II) used as a starting material in FIG. 1 can be produced by the method shown in FIG. 2.

That is, the compound of the formula (II) is produced by reacting a compound of the formula (IX) with a compound of the formula (IV) in an inert solvent in the presence of a dehydrating agent such as N,N'-dicyclohexylcarbodiimide (to be abbreviated as DCC hereinafter) and a base.

In this method, it is preferred to use the compound of the formula (IX) in an amount of 1.0 to 3.0 mol per mole of the compound of the formula (IV). DCC is used preferably in an amount of 1.0 to 1.5 mol per mole of the compound of the formula (IV). The base used together with DCC is not specially limited, while it is preferred to use potassium carbonate or sodium carbonate in an amount of 0.5 to 2.0 mol per mole of the compound of the formula (IV). The inert solvent is not specially limited if it is inert to the reaction, while tert-butyl alcohol, tert-amyl alcohol and isopropyl alcohol are preferred. The reaction temperature can be between room temperature and the boiling point of the solvent, while it is preferably a temperature between 50° and 100° C.

The pyrazole compound of the formula (IX) used as a reaction reagent in the above method can be produced, for example, by the method described in JP-A-61-257974.

Figure 3:
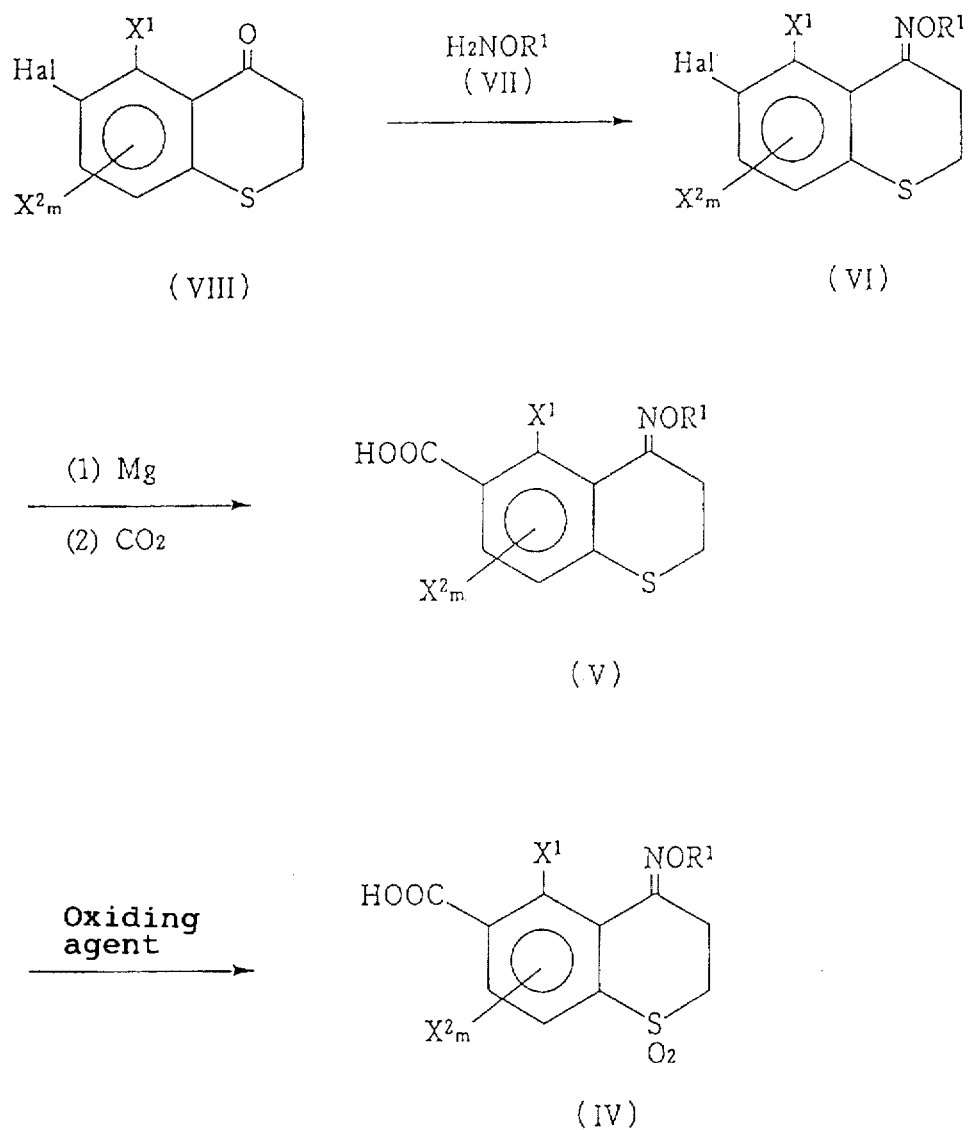
FIG. 3 shows the step of producing the compound of the general formula (IV).

Further, the compound of the formula (IV) used as a starting material in the method shown in FIG. 2 can be produced by the method shown in FIG. 3.

Thiochroman-4-ones of the formula (VIII) used as a starting material in FIG. 3 can be produced by a variety of methods, such as methods described in JP-A-58-198483, International Patent Publication WO088/06155 and Canadian Journal of Chemistry, Vol. 51, page 839 (1973).

In FIG. 3, the synthesis of an oxime (VI) by the conversion of a ketone (VIII) to an oxime is carried out by treating the ketone (VIII) with an alkoxyamine (VII) in water or an organic solvent (e.g., ethanol, methanol or acetic acid) in the presence of an acid catalyst (e.g., hydrochloric acid) or a basic catalyst (e.g., pyridine, aniline, sodium hydroxide or sodium carbonate) at a temperature between 0° C. and the reflux temperature of the solvent (water or organic solvent). For example, the above synthesis is preferably carried out in ethanol in the presence of pyridine at a reflux temperature. In this reaction, the amount of an alkoxyamine (VII) per mole of the ketone (VIII) is preferably 1.0 to 5.0 mol, particularly preferably 1.0 to 2.0 mol.

Then, the obtained oxime (VI) is reacted with magnesium (Mg) to prepare a Grignard reagent, and carbon dioxide ($CO_2$) is reacted therewith to obtain a sulfide included in an aromatic carboxylic acid derivative of the formula (V). As a solvent, it is preferred to use an ether such as diethyl ether or tetrahydrofuran. The reaction temperature is preferably between −78° C. and 50° C., particularly preferably between 0° and 50° C.

The amount of the magnesium (Mg) for preparing the Grignard reagent is preferably 1.0 to 5.0 mol per mole of the oxime (VI). Preferably, the Grignard reaction is smoothly carried out in the co-presence of an alkyl iodide such as methyl iodide or an alkyl bromide such as ethyl bromide. The amount of the alkyl halide used in this case is preferably 0.1 to 3.0 mol per mole of the oxime (VI).

The reaction between the Grignard reagent and carbon dioxide ($CO_2$) is carried out by blowing a carbon dioxide gas from its cylinder or a carbond dioxide gas generated from dry ice (solid carbon dioxide) into the Grignard reagent in the solvent. Further, dry ice may be directly added to the Grignard reagent to allow these to react.

Finally, the sulfur atom is oxidized by using an oxidizing agent in an amount of at least 2 equivalents to form a sulfone, whereby the compound of the formula (IV) is obtained. It is hydrogen peroxide that can be preferably used as an oxidizing agent.

Figure 5:
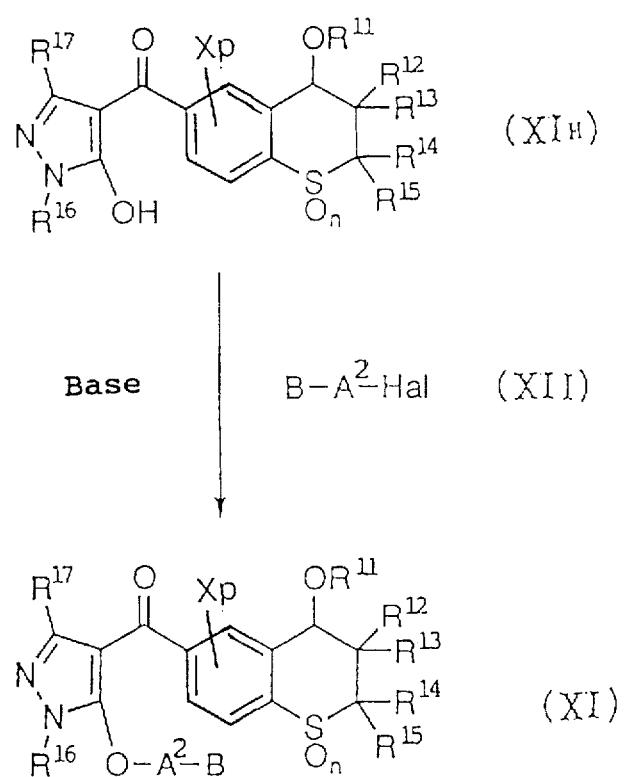
FIG. 5 shows the step of producing the pyrazole derivative of the formula (XI) provided by the present invention.

The novel pyrazole derivative of the formula (XI) provided by the present invention can be produced by the reaction shown in FIG. 5.

In FIG. 5, $R^{11}$, $R^{12}$, $R^{13}$, $R^{14}$, $R^{15}$, $R^{16}$, $R^{17}$, $R^{18}$, $R^{19}$, $X^3$, Y, k, p, m, $A^2$ and B represent those already defined in the general formula (XI), and Hal is a halogen atom.

A starting material of the formula ($XI_H$) is reacted with B—$A^2$—Hal (in which B—$A^2$— represents that which is already defined in the general formula (XI) and Hal is a halogen atom) in an inert solvent in the presence of a base, whereby the pyrazole derivative of the formula (XI) provided by the present invention can be obtained.

In the above step, the molar ratio of the compound of the formula ($XI_H$):the compound of the formula (XII) is preferably 1:1 to 1:3, and for collecting hydrogen halide produced as a byproduct by the reaction, it is preferred to use a base such as sodium carbonate, potassium carbonate, triethylamine or pyridine in an equimolar or greater amount based on the starting material of the formula ($XI_H$). The reaction temperature is preferably between room temperature and the boiling point of a solvent used. The solvent used for the reaction is selected from aromatic hydrocarbons such as benzene and tolune, ether solvents such as diethyl ether, ketone solvents such as methyl ethyl ketone, and halogenated hydrocarbons such as methylene chloride and chloroform. Further a two phases solvent system of the above solvent and water may be used. In this case, a favorable result can be obtained by adding a phase transfer catalyst such as crown ether or benzel chloride triethylammonium to the reaction system.

The pyrazole derivative of the formula ($XI_H$) used as a starting material can be synthesized, for example, by the method described in WO93/18031.

The present invention will be further explained with reference to Examples hereinafter.

PREPARATION EXAMPLES OF COMPOUND (I) OF THE INVENTION

[Preparation Example 1]

A 100-ml eggplant type flask was charged with 1.1 g (2.9 mmol) of 4-methoxyimino-5-methyl-6-(1-ethyl-5-hydroxypyrazol-4-yl) carbonylthiochroman-1,1-dioxide, and 20 ml of methylene chloride was added to prepare a solution. Then, a solution of 0.41 g of potassium carbonate in 20 ml of distilled water was added. Further, a solution of 0.6 g (4.2 mmol) of n-propanesulfonyl chloride as a reaction reagent in 5 ml of methylene chloride was added, and further, 0.05 g of benzyl chloride triethylammonium was added as a catalyst. The resultant mixture was allowed to react by stirring it at room temperature for 24 hours. After the reaction, a methylene chloride layer was separated and dried over anhydrous sodium sulfate, and the methylene chloride was distilled off under reduced pressure. The resultant oily substance was purified through a column packed with silica gel. A mixture of ethyl acetate with n-hexane was used as a developer solvent.

The above operation gave 4-methoxyimino-5-methyl-6-(1-ethyl-5-n-propanesulfonyloxypyrazol-4-yl)-carbonylthiochroman-1,1-dioxide (Compound 1) as a solid in an amount of 0.88 g. The yield was 62 %.

[Preparation Example 2]

4-Methoxyimino-5, 8-dimethyl-6- (1-ethyl-5-n-propanesulfonyloxypyrazol-4-yl) carbonylthiochroman-1,1-dioxide (Compound 2) was obtained at a yield of 48% in the same manner as in Preparation Example 1 except that the starting material was replaced with 4-methoxyimino-5,8-dimethyl-6-(1-ethyl-5-hydroxypyrazol-4-yl)thiochroman-1,1-dioxide.

[Preparation Example 3]

4-Methoxyimino-5,8-dimethyl-6-(1-ethyl-5-p-toluenesulfonyloxypyrazol-4-yl) carbonylthiochroman-1,1-dioxide (Compound 3) was obtained at a yield of 42% in the same manner as in Preparation Example 1 except that the starting material was replaced with 4-methoxyimino-5,8-dimethyl-6-(1-ethyl-5-hydroxypyrazol-4-yl)thiochroman-1,1-dioxide and that p-toluenesulfonyl chloride was used as a reaction reagent.

[Preparation Examples 4–11]

Compounds 4 to 11 were obtained in the same manner as in Preparation Example 1 except that the n-propanesulfonyl chloride as a reaction reagent was replaced with methanesulfonyl chloride, ethansulfonyl chloride, n-butanesulfonyl chloride, n-octanesulfonyl chloride, p-toluenesulfonyl chloride, o-toluenesulfonyl chloride, p-nitrobenzenesulfonyl chloride or p-methoxybenzenesulfonyl chloride.

[Preparation Examples 12–17]

Compounds 12 to 17 were obtained in the same manner as in Preparation Example 1 except that the starting material was replaced with 4-methoxyimino-5,8-dimethyl-6-(1-ethyl-5-hydroxypyrazol-4-yl) carbonylthiochroman-1,1-dioxide and that the reaction regent was replaced with i-propanesulfonyl chloride, n-butanesulfonyl chloride, benzenesulfonyl chloride, p-chlorobenzenesulfonyl chloride, p-fluorobenzenesulfonyl chloride or 3,4-difluorobenzenesulfonyl chloride.

[Preparation Examples 18 and 19]

Compounds 18 and 19 were obtained in the same manner as in Preparation Example 1 except that the starting material was replaced with 4-methoxyimino-5,8-dimethyl-6-(1,3-dimethyl-5-hydroxypyrazol-4-yl) carbonylthiochroman-1,1-dioxide and that n-propanesulfonyl chloride or p-toluenesulfonyl chloride was used as a reaction reagent.

[Preparation Example 20]

A 100-ml eggplant type flask was charged with 0.4 g (1.1 mmol) of 4-methoxyimino-5-methyl-6-(1-ethyl-5-hydroxypyrazol-4-yl) carbonylthiochroman-1,1-dioxide, and 10 ml of methylene chloride was added to prepare a solution. Then, 0.14 g of triethylamine was added. Further, a solution of 0.10 g (1.3 mmol) of acetyl chloride in 5 ml of methylene chloride was added. The mixture was stirred at room temperature for 4 hours to allow it to react. After the reaction, 10 ml of water was added, and a methylene chloride layer was separated, washed with a saturated sodium chloride aqueous solution, and dried over anhydrous sodium sulfate. Then, the methylene chloride was distilled off under reduced pressure. The resultant oily substance was purified through a column packed with silica gel. A mixture of ethyl acetate with n-hexane was used as a developer solvent.

The above operation gave 4-methoxyimino-5-methyl-6-(1-ethyl-5-acetyloxypyrazol-4-yl)carbonylthiochroman-1,1-dioxide (Compound 20).

[Preparation Examples 21–24]

Compounds 21 to 24 were obtained in the same manner as in Preparation Example 20 except that the acetyl chloride was replaced with propionic acid chloride, n-butyric acid chloride, n-valeric acid chloride or n-heptanoyl chloride.

[Preparation Example 25]

Compound 25 was obtained in the same manner as in Preparation Example 20 except that the starting material was replaced with 4-methoxyimino-5,8-dimethyl-6-(1-ethyl-5-hydroxypyrazol-4-yl) carbonylthiochroman-1,1-dioxide and that the reaction reagent was replaced with n-butyric acid chloride.

[Preparation Example 26]

0.4 Gram (1.1 mmol) of 4-methoxyimino-5-methyl-6-(1-ethyl-5-hydroxypyrazol-4-yl) carbonylthiochroman-1,1-dioxide, 0.23 g (1.2 mmol) of phenacyl bromide and 0.15 g of potassium carbonate were added to 10 ml of acetone, and the mixture was stirred under heat for 8 hours. Insolubles were removed by filtration, and then the acetone was distilled off. The remainder was dissolved in ethyl acetate, and the resultant solution was washed with a saturated sodium chloride aqueous solution and then dried over anhydrous sodium sulfate. The ethyl acetate was distilled off under reduced pressure, and the remainder was subjected to column chromatography (hexane/ethyl acetate) to give intended. 4-methoxyimino-5-methyl-6-(1-ethyl-5-phenacyloxypyrazol-4-yl) carbonylthiochroman-1,1-dioxide (Compound 26) at a yield of 52%.

[Preparation Example 27]

Compound 27 was obtained in the same manner as in Preparation Example 26 except that the phenacyl bromide was replaced with chloroacetone.

[Preparation Examples 28 and 29]

Compounds 28 and 29 were obtained in the same manner as in Preparation Example 26 except that the starting material was replaced with 4-methoxyimino-5,8-dimethyl-6-(1-ethyl-5-hydroxypyrazol-4-yl)carbonylthiochroman-1,1-dioxide and that phenacyl bromide or benzyl bromide was used as a reaction reagent.

[Preparation Examples 30 and 31]

4-Ethoxyimino-5-methyl-6-(1-ethyl-5-n-propanesulfonyloxypyrazo 1-4-yl)carbonylthiochroman-1,1-dioxide (Compound 30) and 4-ethoxyimino-5-methyl-6-(1-ethyl-5-p-toluenesulfonyloxypyrazo 1-4-yl)carbonylthiochroman-1,1-dioxide (Compound 31) were obtained at yields of 52% and 37% respectively in the same manner as in Preparation Example 1 except that the starting material was replaced with 4-ethoxyimino-5-methyl-6- (1-ethyl-5-hydroxypyrazol-4-yl) carbonylthiochroman-1,1-dioxide and that n-propanesulfonyl chloride or p-toluenesulfonyl chloride were used as a reaction reagent.

[Preparation Example 32]

4-Ethoxyimino-5-methyl-6-(1-ethyl-5-phenacyloxypyrazol-4-yl) carbonylthiochroman-1,1-dioxide (Compound 32) was obtained at a yield of 28% in the same manner as in Preparation Example 26 except that the starting material was replaced with 4-ethoxyimino-5-methyl-6-(1-ethyl-5-hydroxypyrazol-4-yl)carbonyl thiochroman-1,1-dioxide and that phenacyl bromide was used as a reaction reagent.

[Preparation Example 33]

4-Ethoxyimino-5-methyl-6-(1-ethyl-5-cyclohexanecarbonyloxypyrazol-4-yl)carbonylthiochroman-1,1-dioxide (Compound 33) was obtained at a yield of 50% in the same manner as in Preparation Example 20 except that the starting material was replaced with 4-ethoxyimino-5-methyl-6-(1-ethyl-5-hydroxypyrazol-4-yl) carbonylthiochroman-1,1-dioxide and that the reaction reagent was replaced with cyclohexanecarbonyl chloride.

Tables 1 to 8 show the starting materials, reaction reagents and the structures and yields of the compounds as products in Examples 1 to 33, and Tables 9 to 17 show the physical properties of the obtained compounds.

TABLE 1

| Prep. Ex. No. | Starting material | Reaction reagent | Obtained compound | Y (%)* |
|---|---|---|---|---|
| 1 | [structure] | n-C$_3$H$_7$SO$_2$Cl | [structure] | 62% |
| 2 | [structure] | n-C$_3$H$_7$SO$_2$Cl | [structure] | 48% |
| 3 | the same as the above | CH$_3$-C$_6$H$_4$-SO$_2$Cl | [structure] | 42% |

*Y (%) = yield (percent)

TABLE 2

| Prep. Ex. No. | Starting material | Reaction reagent | Obtained compound | Y (%)* |
|---|---|---|---|---|
| 4 | [structure] | CH$_3$SO$_2$Cl | [structure] | 67% |
| 5 | the same as the above | C$_2$H$_5$SO$_2$Cl | [structure] | 55% |

TABLE 2-continued

| Prep. Ex. No. | Starting material | Reaction reagent | Obtained compound | Y (%)* |
|---|---|---|---|---|
| 6 | the same as the above | n-C$_4$H$_9$SO$_2$Cl | [structure with pyrazole-N-ethyl, O-SO$_2$-C$_4$H$_9$-n, benzoyl bearing CH$_3$, NOCH$_3$, and thiolane-S,S-dioxide] | 72% |
| 7 | the same as the above | n-C$_8$H$_{17}$SO$_2$Cl | [structure with pyrazole-N-ethyl, O-SO$_2$-C$_8$H$_{17}$-n, benzoyl bearing CH$_3$, NOCH$_3$, and thiolane-S,S-dioxide] | 83% |

*Y (%) = yield (percent)

TABLE 3

| Prep. Ex. No. | Starting material | Reaction reagent | Obtained compound | Y (%)* |
|---|---|---|---|---|
| 8 | [pyrazole-OH starting material with N-ethyl, carbonyl linked to benzene bearing CH$_3$, NOCH$_3$, and SO$_2$-containing ring] | H$_3$C–C$_6$H$_4$–SO$_2$Cl | [product with O-SO$_2$-C$_6$H$_4$-CH$_3$] | 71% |
| 9 | the same as the above | o-CH$_3$-C$_6$H$_4$-SO$_2$Cl | [product with O-SO$_2$-(2-CH$_3$-C$_6$H$_4$)] | 85% |
| 10 | the same as the above | O$_2$N–C$_6$H$_4$–SO$_2$Cl | [product with O-SO$_2$-C$_6$H$_4$-NO$_2$] | 83% |

TABLE 3-continued

| Prep. Ex. No. | Starting material | Reaction reagent | Obtained compound | Y (%)* |
|---|---|---|---|---|
| 11 | the same as the above | CH₃O—C₆H₄—SO₂Cl | [structure] | 82% |

*Y (%) = yield (percent)

TABLE 4

| Prep. Ex. No. | Starting material | Reaction reagent | Obtained compound | Y (%)* |
|---|---|---|---|---|
| 12 | [structure] | iPr—SO₂Cl | [structure] | 58% |
| 13 | the same as the above | n-C₄H₉SO₂Cl | [structure] | 79% |
| 14 | the same as the above | C₆H₅—SO₂Cl | [structure] | 84% |
| 15 | the same as the above | Cl—C₆H₄—SO₂Cl | [structure] | 88% |

TABLE 4-continued

| Prep. Ex. No. | Starting material | Reaction reagent | Obtained compound | Y (%)* |
|---|---|---|---|---|
| 16 | the same as the above | F-C₆H₄-SO₂Cl (4-fluoro) | [pyrazole-benzoyl compound with N-ethyl, O-SO₂-(4-F-C₆H₄), thiochromanone N-OCH₃, 2,6-dimethyl, SO₂] | 91% |
| 17 | the same as the above | 3,4-difluoro-C₆H₃-SO₂Cl | [pyrazole-benzoyl compound with N-ethyl, O-SO₂-(3,4-diF-C₆H₃), thiochromanone N-OCH₃, 2,6-dimethyl, SO₂] | 89% |

*Y (%) = yield (percent)

TABLE 5

| Prep. Ex. No. | Starting material | Reaction reagent | Obtained compound | Y (%)* |
|---|---|---|---|---|
| 18 | [3-methyl-5-hydroxy-1-methyl-pyrazole-4-yl benzoyl compound with 2,6-dimethyl, thiochromanone N-OCH₃, SO₂] | n-C₃H₇SO₂Cl | [same with O-SO₂-C₃H₇-n] | 68% |
| 19 | the same as the above | CH₃-C₆H₄-SO₂Cl | [same with O-SO₂-(4-CH₃-C₆H₄)] | 70% |

*Y (%) = yield (percent)

TABLE 6

| Prep. Ex. No. | Starting material | Reaction reagent | Obtained compound | Y (%)* |
|---|---|---|---|---|
| 20 | [structure: pyrazole-OH, CH₃, NOCH₃, SO₂ thiochroman ketone] | CH₃COCl | [structure: O-C(=O)-CH₃ ester] | 45% |
| 21 | the same as the above | C₂H₅COCl | [structure: O-C(=O)-C₂H₅ ester] | 61% |
| 22 | the same as the above | n-C₃H₇COCl | [structure: O-C(=O)-C₃H₇-n ester] | 74% |
| 23 | the same as the above | n-C₄H₉COCl | [structure: O-C(=O)-C₄H₉-n ester] | 53% |
| 24 | the same as the above | n-C₆H₁₃COCl | [structure: O-C(=O)-C₆H₁₃-n ester] | 69% |
| 25 | [structure: pyrazole-OH, CH₃, NOCH₃, SO₂, additional CH₃] | n-C₃H₇COCl | [structure: O-C(=O)-C₃H₇-n ester with extra CH₃] | 78% |

*Y (%) = yield (percent)

TABLE 7

| Prep. Ex. No. | Starting material | Reaction reagent | Obtained compound | Y (%)* |
|---|---|---|---|---|
| 26 | (pyrazole-OH, ethyl N, with benzoyl-aryl-CH3, NOCH3, thiochroman SO2) | C6H5-COCH2Br | (O-CH2-CO-C6H5 ether product) | 51% |
| 27 | the same as the above | CH3COCH2Cl | (O-CH2COCH3 ether product) | 41% |
| 28 | (pyrazole-OH, ethyl N, with benzoyl-2,6-dimethyl-aryl, NOCH3, thiochroman SO2) | C6H5-COCH2Br | (O-CH2CO-C6H5 ether product) | 57% |
| 29 | the same as the above | C6H5-CH2Br | (O-CH2-C6H5 benzyl ether product) | 65% |

*Y (%) = yield (percent)

TABLE 8

| Prep. Ex. No. | Starting material | Reaction reagent | Obtained compound | Y (%)* |
|---|---|---|---|---|
| 30 | (pyrazole-OH, ethyl N, CH3, NOC2H5, thiochroman SO2) | C3H7SO2Cl | (O-SO2-C3H7-n ester product) | 52 |

TABLE 8-continued

| Prep. Ex. No. | Starting material | Reaction reagent | Obtained compound | Y (%)* |
|---|---|---|---|---|
| 31 | the same as the above | H3C—⟨C6H4⟩—SO2Cl | (structure with tosyl group) | 37 |
| 32 | the same as the above | PhC(O)CH2Br | (structure with phenacyl group) | 28 |
| 33 | the same as the above | cyclohexyl-COCl | (structure with cyclohexanecarbonyl group) | 50 |

*Y (%) = yield (present)

TABLE 9

| Prep. Ex. No. | Compound No. | NMR (ppm) Internal Standard tetramethyl-silane Solvent deutero-chroroform | IR (cm$^{-1}$) | melting point (°C.) |
|---|---|---|---|---|
| 1 | 1 | 1.18(3H, t) 1.52(3H, t) 2.0–2.2(2H, m) 2.52(3H, s) 3.35(4H, t) 3.73(2H, t) 4.06(3H, s) 4.23(2H, q) 7.45(H, s) 7.48(H, d) 7.96(H, d) | 3000,2960 1665 1135,1325 1190,1395 | 146.0–150.7 |
| 2 | 2 | 1.18(3H, t) 1.52(3H, t) 2.0–2.2(2H, m) 2.43(3H, s) 2.73(3H, s) 3.35(4H, t) 3.73(2H, t) 4.02(3H, s) | 3000,2970 1670 1130,1325 1180,1395 | 158.8–162.1 |

TABLE 9-continued

| Prep. Ex. No. | Compound No. | NMR (ppm) Internal Standard tetramethyl-silane Solvent deutero-chroroform | IR (cm$^{-1}$) | melting point (°C.) |
|---|---|---|---|---|
| 3 | 3 | 4.23(2H, q) 7.09(H, s) 7.47(H, s) 1.51(3H, t) 2.39(3H, s) 2.47(3H, s) 2.67(3H, s) 3.34(4H, t) 4.02(3H, s) 4.20(2H, q) 7.03(H, s) 7.40(2H, d) 7.52(H, s) 7.91(2H, d) | 2980,2940 1665 1120,1310 1180,1390 | glass-like substance |

TABLE 10

| Prep. Ex. No. | Comp. No. | NMR (ppm) Internal Standard tetramethyl-silane Solvent deutero-chroroform | IR (cm$^{-1}$) | melting point (°C.) |
|---|---|---|---|---|
| 4 | 4 | 1.52(3H, t), 2.52(3H, S) 3.3–3.4(4H, m) 3.65(3H, s), 4.07, (3, s) | 2950 1660 1320 | — |

TABLE 10-continued

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| | | 4.23(2H, q), 7.42(1H, s) 7.46(1H, d). 7.95(1H, d) | 1190 | |
| 5 | 5 | 1.52(3H, t), 1.66(3H, t) 2.52(3H, s), 3.3–3.5(4H, m) 3,79(2H, q), 4.07(3H, s) 4.25(2H, q), 7.44(1H, s) 7.46(1H, d), 7.94(1H, d) | 2980 1670 1320 1190 | — |
| 6 | 6 | 1.02(3H, t) 1.51(3H, t) 1.5–2.2(4H, m), 2.52(3H, s) 3.2–3.5, (4H, m), 3.6–3.9(2H, m) 4.05(3H, s), 4.23(2H, q) 7.43(1H, s) 7.46(1H, d) 7.95(1H, d) | 2950 1660 1320 1130 | 151.9–155.8 |
| 7 | 7 | 0.89(3H, t), 1.1–1.7(12H, m) 2.52(3H, s), 3.3–3.5(4H, m) 3.6–3.9(2H, m), 4.07(3H, s) 4.23(2H, q), 7.44(1H, s) 7.46(1H, d), 7.96(1H, d) | 2940 1660 1320 1120 | — |

TABLE 11

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 8 | 8 | 1.49(3H, t), 2.47(3H, s) 2.49(3H, s), 3.3–3.5(4H, m) 4.05(3H, s), 4.17(2H, q) 7.35(1H, s), 7.4–8.0(6H, m) | 2950 1680 1320 1130 | glass-like |
| 9 | 9 | 1.50(3H, t), 2.0–2.9(6H, m) 3.2–3.4(4H, m), 4.05(3H, s) 4.19(2H, q), 7.2–8.0(7H, m) | 2970 1680 1330 1140 | — |
| 10 | 10 | 1.56(3H, t), 2.44(3H, s) 3.3–3.5(4H, m), 4.07(3H, s) 4.28(2H, q), 7.33(1H, d) 7.39(1H, s), 7.90(1H, d) 8.40(4H, ABq) | 2970 1660 1320 1130 | 187 (Decompose) |
| 11 | 11 | 1.50(3H, t), 2.50(3H, s) 3.2–3.4(4H, m), 3.90(3H, s) 4.03(3H, s), 4.19(2H, q) 7.02(2H, d), 7.31(1H, d) 7.54(1H, s), 7.87(1H, d) 7.90(2H, d) | 2950 1660 1320 1120 | glass-like |

TABLE 12

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 12 | 12 | 1.52(3H, t), 1.61(6H, d) 2.43(3H, s), 2.72(3H, s) 3.3–3.5(4H, m), 4.02(3H, s) 4.22(2H, q), 7.19(1H, s) 7.50(1H, s) | 2980 1670 1320 1130 | 180.4–182.2 |
| 13 | 13 | 1.01(3H, t), 1.4–1.7(5H, m) 1.8–2.3(2H, m), 2.43(3H, s) 2.72(3H, s), 3.2–3.5(4H, m) 3.6–3.9(2H, m), 4.02(3H, s) 4.22(2H, q), 7.18(1H, s) 7.46(1H, s) | 2950 1660 1320 1120 | 171.7–176.6 |
| 14 | 14 | 1.51(3H, t), 2.39(3H, s) 2.66(2H, s), 3.2–3.4(4H, m) 4.01(3H, s), 4.19(2H, q) 7.04(1H, s), 7.53(1H, s) 7.5–8.2(5H, m) | 2950 1660 1310 1120 | — |
| 15 | 15 | 1.53(3H, t), 2.37(3H, s) 2.68(3H, s), 3.2–3.5(4H, m) 4.02(3H, s), 4.24(2H, q) 7.04(1H, s), 7.50(1H, s) 7.60(2H, d), 8.01(2H, d) | 2960 1670 1320 1140 | — |
| 16 | 16 | 1.54(3H, t), 2.39(3H, s) 2.69(3H, s), 3.3–3.5(4H, m) 4.02(3H, s), 4.24(2H, q) 7.06(1H, s), 7.2–7.4(2H, m) 7.52(1H, s), 8.0–8.2(2H, m) | 2950 1670 1310 1130 | — |

TABLE 13

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 17 | 17 | 1.54(3H, t), 2.38(3H, s) 2.69(3H, s), 3.2–3.5(4H, m) 4.02(3H, s), 4.26(2H, q) 7.07(1H, m), 7.2–7.5(1H, m) 7.49(1H, s), 7.8–8.1(2H, m) | 2950 1670 1320 1140 | 189.2–191.4 |
| 18 | 18 | 1.09(3H, t), 1.7–2.1(2H, m) 2.08(3H, s), 2.42(3H, s) 2.72(3H, s), 3.1–3.4(6H, m) 3.81(3H, s), 4.02(3H, s) 7.15(1H, s) | 2970 1660 1330 1140 | — |
| 19 | 19 | 2.24(3H, s), 2.46(6H, s) 2.61(3H, s), 3.3–3.5(4H, m) 3.66(3H, s), 4.02(3H, s) 7.02(1H, s), 7.35(2H, d) 7.62(2H, d) | 2950 1650 1320 1120 | — |

TABLE 14

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 20 | 20 | 1.45(3H, t), 2.31(3JH, s) 2.50(3H, s), 3.2–3.4(4H, m) 4.02(2H, q), 4.06(3H, s) 7.42(1H, d), 7.57(1H, s) 7.92(1H, d) | 2950 1790 1660 1320 1120 | — |
| 21 | 21 | 1.23(3H, t), 1.45(3H, t) 2.50(3H, s), 2.59(2H, q) 3.3–3.5(4H, m), 4.01(2H, q) 4.06(3H, s), 7.40(1H, d) 7.58(1H, s), 7.93(JH, d) | 2960 1800 1670 1320 1130 | — |
| 22 | 22 | 1.03(3H, t), 1.43(3H, t) 1.6–2.0(2H, m), 2.50(3H, s) 2.54(2H, t), 3.3–3.5(4H, m) 4.02(2H, q), 4.07(3H, s) 7.41(1H, d), 7.48(IH, s) 7.96(1H, d) | 2970 1800 1670 1330 1130 | — |
| 23 | 23 | 0.97(3H, t), 1.1–1.9(4H, m) 1.43(3H, t), 2.50(3H, s) 2.56(2H, t), 3.2–3.5(4H, m) 4.02(2H, q), 4.07(3H, s) 7.41(1H, d), 7.57(1H, s) 7.93(1H, d) | 2950 1800 1660 1320 1130 | — |
| 24 | 24 | 0.90(3H, t), 1.1–2.0(8H, m) 1.43(3H, t), 2.49(3H, s) 2.57(2H, t), 3.2–3.5(4H, m) 4.02(2H, q), 4.06(3H, s) 7.41(1H, d), 7.56(2H, s) 7.94(1H, s) | — | — |

TABLE 15

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 25 | 25 | 1.03(3H, t), 1.44(3H, t) 1.5–2.0(2H, m), 2.40(3H, s) 2.53(2H, t), 2.70(3H, s) 3.2–3.5(4H, m), 4.02(3H, s) 4.02(2H, q), 7.12(1H, s) 7.59(1H, s) | 2940 1790 1660 1310 1110 | — |

TABLE 16

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 26 | 26 | 1.51(3H, t), 2.41(3H, s) 3.2–3.4(4H, m), 4.02(3H, s) 4.28(2H, q), 6.19(2H, s) 7.19(1H, s), 7.3–8.1(7H, m) | 2950 1710 1650 1320 1130 | — |
| 27 | 27 | 1.47(3H, t), 2.22(3H, s) 2.48(3H, s), 3.3–3.5(4H, m) 4.05(3H, s), 4.19(2H, q) 5.44(2H, s), 7.18(1H, s) 7.39(1H, d), 7.94(1H, d) | 2950 1740 1650 1320 1110 | — |
| 28 | 28 | 1.53(3H, t), 2.32(3H, s) 2.70(3H, s), 3.2–3.4(4H, m) 4.00(3H, s), 4.30(2H, q) 6.19(2H, s), 7.10(1H, s) 7.2–8.0(6H, m) | — | — |
| 29 | 29 | 1.25(3H, t), 2.45(3H, s) 2.71(3H, s), 3.2–3.4(4H, m) 3.92(2H, q), 4.02(3H, s) 5.59(2H, s), 7.14(1H, s) 7.28(1H, s), 7.38(5H, s) | 2950 1650 1310 1130 | 176.5–179.2 |

TABLE 17

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 30 | 30 | 1.18(3H,t), 1.34(3H, t), 1.52(3H, t) 1.9–2.4(2H, m), 2.52(3H, s) 3.2–3.5(4H, m), 3.6–3.9(2H, m) 4.22(2H, q), 4.30(2H, q), 7.45(1H, s) 7.71 2H, dd) | 2950 1660 1170 | — |
| 31 | 31 | 1.33(3H, t), 1.50(3H, t), 2.48(6H, s) 3.2–3.5(4H, m), 4.17(2H, q) 4.29(2H, q), 7.35(1H,s),T.6T(6H,dd) | 2950 1670 1170 | — |
| 31 | 31 | 1.33(3H, t), 1.43(3H, t), 1.3–2.2(11H, m) 2.48(3H, s), 3.2–3.5(4H, m) 4.01(2H, q), 4.27(2H, q), 7.60(1H, s) 7.66(2H, dd) | 3000 1710 1640 1130 | — |

TABLE 17-continued

| Prep. Ex. No. | Comp. No. | NMR (ppm) Internal Standard tetramethyl-silane Solvent deutero-chroroform | IR (cm⁻¹) | melting point (°C.) |
|---|---|---|---|---|
| 33 | 33 | 1.32(3H, t), 1.52(3H, t), 2.41(3H, s) 3.2–3.5(4H, m), 4.27(2H, q) 4.28(2H, q), 6.20(2H, s), 7.2–8.1(8H, m) | 3000 1800 1660 1130 | — |

PREPARATION EXAMPLES OF COMPOUND (XI) OF THE INVENTION

[Preparation Example 51]

4-Methoxy-5-methyl-6-(1-ethyl-5-hydroxypyrazol-4-yl) carbonylthiochroman-1,1-dioxide was used as a starting material (XI$_H$). And, 0.40 g (1.1 mmol) thereof was dissolved in 4 ml of methylene chloride, and 0.22 g (2.2 mmol) of triethylamine as a base and 0.17 g (2.2 mmol) of acetyl chloride as a reaction reagent (XII) were added. The resultant mixture was allowed to react at room temperature for 8 hours. A saturated sodium carbonate aqueous solution was added to the reaction mixture, the reaction mixture was extracted with ethyl acetate, and its organic layer was dried over anhydrous sodium sulfate. The solvent was distilled off under reduced pressure, and the resultant oil was purified with flush column chromatography (Wako Gel C-300: hexane/ethyl acetate=1:2) to give 0.33 g (yield 73%) of 4-methoxy-5-methyl-6-(1-ethyl-5-acetoxypyrazol-4-yl) carbonylthiochroman-1,1-dioxide (Compound No. 51) as an end compound which comes under the general formula (XI). Table 18 shows the structures of the starting material (XI$_H$) and the reaction reagent (XII), and the structure and the yield of the end product (XI).

[Preparation Examples 52–58]

Compounds Nos. 52 to 58 shown in Tables 18 and 19 were obtained in the same manner as in Example 51 except that the acetyl chloride as a reaction reagent (XII) was replaced with reaction reagents shown in Tables 18 and 19 and that the starting materials shown in Tables 18 and 19 were used as a starting material (XI$_H$).

TABLE 18

| Prep. Ex. No. | Reaction reagent (XII) | Starting material (XI$_H$) | Pyrazole Deriv. as end product (XI) | Y (%)* |
|---|---|---|---|---|
| 51 | CH$_3$—C(=O)—Cl | [structure] | compound No.51 | 73 |
| 52 | Et—C(=O)—Cl | [structure] | compound No.52 | 51 |
| 53 | [propyl]—C(=O)—Cl | [structure] | compound No.53 | 61 |

TABLE 18-continued
| Prep. Ex. No. | Reaction reagent (XII) | Starting material (XI_H) | Pyrazole Deriv. as end product (XI) | Y (%)* |
|---|---|---|---|---|
| 54 | 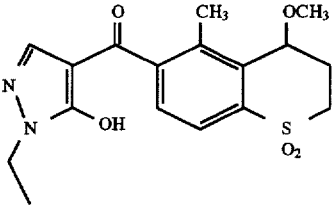 | 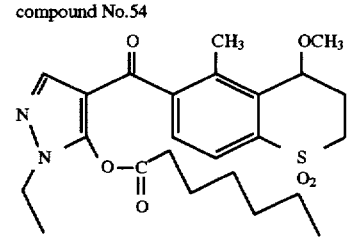 | compound No.54 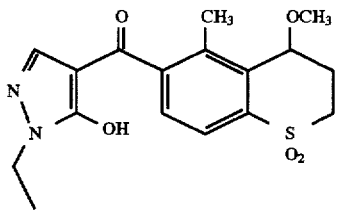 | 75 |
*Y (%) = yield (present)
TABLE 19
| Prep. Ex. No. | Reaction reagent (XII) | Starting material (XI_H) | Pyrazole Deriv. as end product (XI) | Y (%)* |
|---|---|---|---|---|
| 55 | 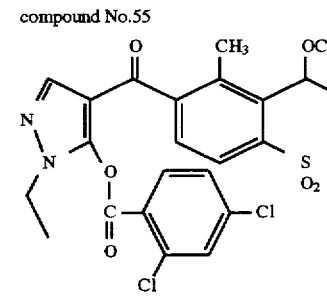 | 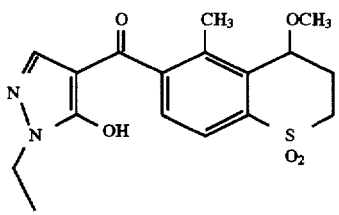 | compound No.55 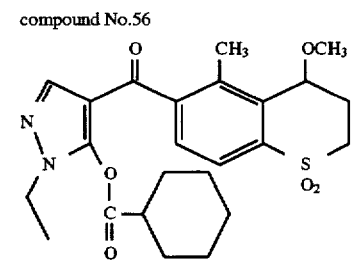 | 49 |
| 56 | 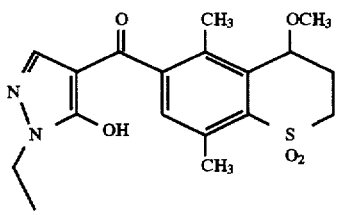 | 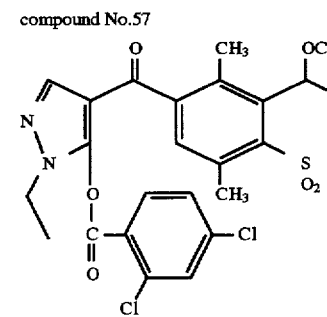 | compound No.56 | 54 |
| 57 | | | compound No.57 | 57 |

TABLE 19-continued

| Prep. Ex. No. | Reaction reagent (XII) | Starting material (XI_H) | Pyrazole Deriv. as end product (XI) | Y (%)* |
|---|---|---|---|---|
| 58 | cyclohexyl-C(=O)-Cl | [structure: pyrazole with N-ethyl, OH, linked to C(=O)-aryl(CH3, OCH3, CH3) with thiochroman-S-O2] | compound No.58 [structure: product with O-C(=O)-cyclohexyl group] | 63 |

*Y (%) = yield (percent)

[Preparation Example 59]

4-Methoxy-5-methyl-6-(1-ethyl-5-hydroxypyrazol-4-yl)carbonylthiochroman-1,1-dioxide was used as a starting material (XI_H). And, 0.4 g (1.10 mmol) thereof was dissolved in 10 ml of methyl ethyl ketone, and 0.15 g (1.10 mmol) of bromoacetone as a reaction reagent (XII) and 0.30 g (2.20 mmol) of potassium carbonate as a base were added. The resultant mixture was refluxed under heat for 3 hours. Water was added to the reaction mixture, and the reaction mixture was extracted with ethyl acetate. Its organic layer was separated, and dried over anhydrous sodium sulfate. Then, the solvent was distilled off under reduced pressure, and the resultant oil was purified with flush column chromatography (Wako Gel C-300: hexane/ethyl acetate=1:2) to give 0.29 g (yield 63%) of 4-methoxy-5-methyl-6-(5-acetylmethyloxy-1-ethylpyrazol-4-yl)carbonylthiochroman-1, 1-dioxide (Compound No. 59) as an end compound which comes under the general formula (XI). Table 20 shows the structures of the starting material (XI_H) and the reaction reagent (XII), and the structure and the yield of the end product (XI).

[Preparation Examples 60–61]

Compounds Nos. 60 and 61 shown in Table 20 were obtained in the same manner as in Example 59 except that the bromoacetone as a reaction reagent (XII) was replaced with reaction reagents shown in Table 20 and that the starting materials shown in Table 20 were used.

TABLE 20

| Prep. Ex. No. | Reaction reagent (XII) | Starting material (XI_H) | Pyrazole Deriv. as end product (XI) | Y (%)* |
|---|---|---|---|---|
| 59 | CH₃—C(=O)—CH₂—Br | [structure: pyrazole N-ethyl, OH, C(=O)-aryl(CH3, OCH3)-thiochroman-SO2] | compound No.59 [structure with OCH₂—C(=O)—CH₃] | 63 |
| 60 | Ph—C(=O)—CH₂—Br | [structure: pyrazole N-ethyl, OH, C(=O)-aryl(CH3, OCH3)-thiochroman-SO2] | compound No.60 [structure with O—CH₂C(=O)—Ph] | 19 |

TABLE 20-continued

| Prep. Ex. No. | Reaction reagent (XII) | Starting material (XI_H) | Pyrazole Deriv. as end product (XI) | Y (%)* |
|---|---|---|---|---|
| 61 | Ph—C(=O)—CH₂—Br | [structure] | compound No.61 [structure] | 39 |

*Y (%) = yield (present)

[Preparation Example 62]

4-Methoxy-5-methyl-6-(1-ethyl-5-hydroxypyrazol-4-yl) carbonylthiochroman-1,1-dioxide was used as a starting material (XI_H). And, 0.4 g (1.10 mmol) thereof was dissolved in 5 ml of acetone, and 0.21 g (1.21 mmol) of benzyl bromide as a reaction reagent (XII) and 0.15 g (1.10 mmol) of potassium carbonate as a base were added. The resultant mixture was refluxed under heat for 3 hours. Water was added to the reaction mixture, and the reaction mixture was extracted with ethyl acetate. Its organic layer was separated, and dried over anhydrous sodium sulfate. Then, the solvent was distilled off under reduced pressure, and the resultant oil was purified with flush column chromatography (Wako Gel C-300: hexane/ethyl acetate=2:3) to give 0.37 g (yield 74%) of 4-methoxy-5-methyl-6-(5-benzyloxy-1-ethylpyrazol-4-yl) carbonylthiochroman-1,1-dioxide (Compound No. 62) as an end compound which comes under the general formula (XI). Table 21 shows the structures of the starting material (XI_H) and the reaction reagent (XII), and the structure and the yield of the end product (I).

solved in 6 ml of methylene chloride, a solution of 0.30 g (2.20 mmol) of potassium carbonate as a base in 4 ml of water was added, and 0.29 g (1.30 mmol) of p-nitrobenzenesulfonyl chloride and 0.05 g (0.2 mmol) of chlorobenzyltriethylammonium chloride as reaction reagents (XII) were added. The resultant mixture was allowed to react at room temperature for 2 hours. Further, the reaction mixture was refluxed under heat for 2 hours. After the reaction mixture was allowed to cool, its methylene chloride layer was separated, and dried over anhydrous sodium sulfate. Then, the solvent was distilled off under reduced pressure, and the resultant oil was purified with flush column chromatography to give 0.42 g (yield 70%) of 4-methoxy-5-methyl-6-(1-ethyl-5-(p-nitrobenzenesulfonyl) oxypyrazol-4-yl)carbonylthiochroman-1,1-dioxide (Compound No. 13) as an end compound which comes under the general formula (XI). Table 22 shows the structures of the starting material (XI_H) and the reaction reagent (XII), and the structure and the yield of the end product (XI).

[Preparation Examples 64–65]

TABLE 21

| Prep. Ex. No. | Starting material (XII) | Reaction reagent (XI_H) | Pyrazole Deriv. as end product (XI) | Y (%)* |
|---|---|---|---|---|
| 62 | Ph.CH₂.Br | [structure] | compound No.62 [structure] | 74 |

*Y (%) = yield (percent)

[Preparation Example 63]

4-Methoxy-5-methyl-6-(1-ethyl-5-hydroxypyrazol-4-yl) carbonylthiochroman-1,1-dioxide was used as a starting material (XI_H). And, 0.4 g (1.10 mmol) thereof was dis- Compounds Nos. 64 and 65 shown in Table 22 were obtained in the same manner as; in Example 63 except that the p-nitrobenzenesulfonyl chloride as a reaction reagent (XII) was replaced with reaction reagents shown in Table 22.

TABLE 22

| Prep. Ex. No. | Reaction regent (II) | Starting material (XI$_H$) |
|---|---|---|
| 63 | O$_2$N–C$_6$H$_4$–SO$_2$Cl | (ketone-pyrazole structure with CH$_3$, OCH$_3$, SO$_2$) |
| 64 | CH$_3$O–C$_6$H$_4$–SO$_2$Cl | (ketone-pyrazole structure with CH$_3$, OCH$_3$, SO$_2$) |
| 65 | CH$_3$(CH$_2$)$_7$SO$_2$Cl | (ketone-pyrazole structure with CH$_3$, OCH$_3$, SO$_2$) |

| Prep. Ex. No. | Pyrazole Derv. as end product (I) | Y (%)* |
|---|---|---|
| 63 | compound No.63 | 70 |
| 64 | compound No.64 | 85 |
| 65 | compound No.63 | 62 |

*Y (%) = yield (percent)

Tables 23, 24 and 25 show NMR and IR analysis results of Compounds Nos. 51 to 65 obtained in the above Preparation Examples 51 to 65.

TABLE 23

| Comp. No. | NMR (ppm) Int. Std.*: tetramethylsilane Solvent: deutero-chroroform | IR (cm$^{-1}$) KBr tablet |
|---|---|---|
| 51 | 1.43(3H, t, J=7.3Hz) 2.26(3H, s) | 2970 |
|    | 2.33(3H, s) 2.4–2.9(2H, m) | 1810 |
|    | 3.1–3.4(1H, m) 3.48(3H, s) | 1670 |
|    | 3.6–3.8(1H, m) 4.02(2H, q, J–7.3Hz) | 1300 |
|    | 4.53(1H, t, J=2.9HZ) 7.45(1H, d, J=8.1Hz) | 1140 |
|    | 7.59(1H, s) 7.89(1H, d, J=8.1Hz) | |
| 52 | 1.21(3H, t) 1.44(3H, t, J=7.3Hz) | 2960 |
|    | 2.33(3H, s) 2.54(2H, q) | 1800 |
|    | 2.4–2.9(2H, m) 3.1–3.4(1H, m) | 1670 |
|    | 3.47(3H, s) 3.6–3.8(1H, m) | 1300 |
|    | 4.02(2H, q J=7.3Hz) 4.53(1H, t) | 1140 |
|    | 7.45(1H, d, J=8.2Hz) 7.59(1H, s) | |
|    | 7.87(1H, d, J=8.2Hz) | |
| 53 | 0.96(3H, t) 1.43(3H, t, J=7.3Hz) | 2970 |
|    | 1.3–1.8(4H, m) 2.33(3H, s) | 1800 |
|    | 2.51(2H, t, J=7.5Hz) 2.6–2.8(2H, m) | 1670 |
|    | 3.1–3.3(1H, m) 3.47(3H, s) | 1300 |
|    | 3.6–3.8(1H, m) 4.01(2H, q, J=7.3Hz) | 1140 |
|    | 4.52(1H, t, J=2.9Hz) 7.45(1H, d, J=8.2Hz) | |
|    | 7.58(1H, s) 7.87(1H, d, J=8.2Hz) | |
| 54 | 0.90(3H, t) 1,43(3H, t, J=7.3Hz) | 2950 |
|    | 1.2–1.8(8H, m) 2.33(3H, s) | 1800 |
|    | 2.51(2H, t, J=7.6Hz) 2.5–2.9(2H, m) | 1660 |
|    | 3.1–3.4(1H, m) 3.47(3H, s) 3.6–3.8(1H, m) | 1300 |
|    | 4.01(2H, q, J=7.3Hz) 4.52(1H, t, J=2.9Hz) | 1130 |
|    | 7.45(1H, d, J=8.3Hz) 7.57(1H, s) | |
|    | 7.87(1H, d, J=8.3Hz) | |
| 55 | 1.48(3H, t, J=7.3Hz) 2.31(3H, s) | 2950 |
|    | 2.4–2.8(2H, m) 3.0–3.3(1H, m) | 1790 |
|    | 3.44(3H, s) 3.5–3.7(1H, m) | 1670 |
|    | 4.09(2H, q, J=7.5Hz) 4.43(1H, t, J=2.9Hz) | 1300 |
|    | 7.3–7.9(5H, m) | 1140 |

*Int. Std. = Internal Standard

TABLE 24

| Comp. No. | NMR (ppm) Int. Std*: tetramethylsilane Solvent: deutero-chroroform | IR (cm$^{-1}$) KBr tablet |
|---|---|---|
| 56 | 1.42(3H, t, J=7.3Hz) 1.3–2.0(10H, m) | 2970 |
|    | 2.33(3H, s)2.3–2.8(3H, m) | 1800 |
|    | 3.1–3.3(1H, m) 3.47(3H, s) | 1670 |
|    | 3.6–3.8(1H, m) 3.99(2H, q, J=7.3Hz) | 1300 |
|    | 4.52(1H, t, J=2.9Hz) 7.44(1H, d, J=8.2Hz) | 1140 |
|    | 7.61(1H, s) 7.86(1H, d, J=8.2Hz) | |
| 57 | 1.49(3H, t) 2.25(3H, s) | 2950 |
|    | 2.3–2.7(2H, m) 2.69(3H, s) | 1780 |
|    | 3.1–3.3(1H, m) 3.43(3H, s) | 1660 |
|    | 3.4–3.7(1H, m) 4.10(2H, q) | 1295 |
|    | 4.40(1H, t) 7.2–7.9(5H, m) | 1135 |
| 58 | 1.2–2.0(10H, m) 1.42(3H, t, J=7.3Hz) | 2960 |
|    | 2.27(3H, s) 2.3–2.6(3H, s) | 1800 |
|    | 2.73(3H, s)3.1–3.3(1H, m) | 1670 |
|    | 3.45(3H, s) 3.7–3.9(1H, m) | 1300 |
|    | 3.98(2H, q, J=7.3Hz) 4.48(1H, m) | 1140 |
|    | 7.18(1H, s) 7.68(1H, s) | |
| 59 | 1.46(3H, t, J=7.3Hz) 2.30(3H, S) | 2950 |
|    | 2.44(3H, s) 2.6–2.8(2H, m) | 1750 |
|    | 3.1–3.3(1H, m) 3.47(3H, s) | 1660 |
|    | 3.6–3.7(1H, m) 4.17(2H, q, J=7.3Hz) | 1320 |
|    | 4.51(1H, t) 5.41(2H, s) 7.16(1H, s) | 1140 |
|    | 7.42(1H, d, J=8.2Hz) 7.86(1H, d, J=8.2Hz) | |

TABLE 24-continued

| Comp. No. | NMR (ppm) Int. Std*: tetramethylsilane Solvent: deutero-chroroform | IR (cm$^{-1}$) KBr tablet |
|---|---|---|
| 60 | 1.52(3H, t, J=7.3Hz) 2.27(3H, s) | 2950 |
|    | 2.6–2.8(2H, m) 3.1–3.3(1H, m) | 1720 |
|    | 3.45(3H, s) 3.5–3.7(1H, m) | 1669 |
|    | 4.29(2H, q, J=7.3Hz) 4.49(1H, t) | 1300 |
|    | 6.17(2H, s)7.2–8.0(8H, m) | 1140 |

*Int. Std. = Internal Standard

TABLE 25

| Comp. No. | NMR (ppm) Int. Std.*: tetramethylsilane Solvent: deutero-chroroform | IR (cm$^{-1}$) KBr tablet |
|---|---|---|
| 61 | 1.52(3H, t) 2.22(3H, s) | 2950 |
|    | 2.3–2.6(2H, m) 2.70(3H, s) | 1710 |
|    | 3.1–3.3(1H, m) 3.43(3H, s) | 1650 |
|    | 3.6–3.9(1H, m) 4.30(2H, q) | 1290 |
|    | 4.45(1H, t) 6.18(2H, s) | 1180 |
|    | 7.1–8.0(7H, m) | |
| 62 | 1.26(3H, t, J=7.3Hz) 2.38(3H, s) | 2960 |
|    | 2.6–2.8(2H, m) 3.1–3.4(1H, m) | 1660 |
|    | 3.49(3H, s) 3.6–3.8(1H, m) | 1300 |
|    | 3.92(2H, q, J=7.3Hz) 4.54(1H, t) | 1140 |
|    | 5.58(2H, s) 7.2–7.3(1H, m) | |
|    | 7.3–7.5(6H, m) 7.88(1H, d, J=8.2Hz) | |
| 63 | 1.60(3H, t, J=7.3Hz) 2.31(3H, s) | 2960 |
|    | 2.5–2.8(2H, m) 3.1–3.4(1H, m) | 1670 |
|    | 3.49(3H, s) 3.6–3.8(1H, m) | 1550 |
|    | 4.28(2H, q, J=7.3Hz) 4.51(1H, t, J=7.3Hz) | 1360 |
|    | 4.51(1H, t, t, J=2.9Hz) 7.38(1H, d, J=8.2Hz) | 1300 |
|    | 7.56(1H, s) 7.78(1H, d, J=8.2Hz) | 1140 |
|    | 8.20(2H, d, J=9.3Hz) 8.45(2H, d, J=9.3Hz) | 870 |
| 64 | 1.51(3H, t, J=7.2Hz) 2.36(3H, s) | 2960 |
|    | 2.6–2.8(2H, m) 3.1–3.4(1H, z) | 1670 |
|    | 3.48(3H, s) 3.6–3.8(1H, m) | 1300 |
|    | 3.88(3H, s) 4.17(2H, q, J=7.3Hz) | 1140 |
|    | 4.54(1H, t, J=2.7Hz) 7.03(2H, d, J=9.3Hz) | |
|    | 7.34(1H, d, J=8.4Hz) 7.55(1H, s) | |
|    | 7.79(1H, d, J=8.4Hz) 7.83(2H, d, J=9.3Hz) | |
| 65 | 0.8–1.0(3H, m) 1.2–1.6(10H, m) | 2950 |
|    | 1.51(3H, t, J=7.3Hz) 2.1–2.2(2H, m) | 1670 |
|    | 2.37(3H, s) 2.6–2.9(2H, m) | 1300 |
|    | 3.1–3.3(1H, m) 3.48(3H, s) | 1140 |
|    | 3.6–3.8(3H, m) 4.22(2H, q, J=7.3Hz) | |
|    | 4.54(1H, t) 7.5–7.6(2H, m) | |
|    | 7.89(1H, d, J=8.4Hz) | |

*Int. Std. = Internal Standard

HERBICIDE EXAMPLES (1) Preparation of herbicide containing pyrazole compound of the formula (I)

97 Parts by weight of talc (trade name: Zeaklite) as a carrier, 1.5 parts by weight of alkylarylsulfonic acid (trade name: Neoplex, supplied by Kao-Atlas K. K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier and 10 parts by weight of one of compounds of formula (I) of the present invention obtained in the above Preparation Examples (Compounds 1 to 33) (or 10 parts by weight of one of the following Compounds A, B and C (Compound A: Compound No. 35 in JP-A-2-173, Compound B: Compound No. 1 in JP-A-63-122627 and Compound C: Compound No. 66 in PCT/JP93/00274 (WO/9318031) for Comparative Examples) were uniformly pulverized and mixed to obtain a herbicide.

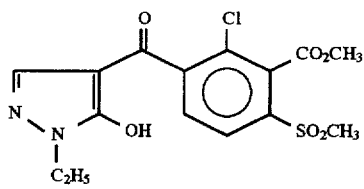

(A)

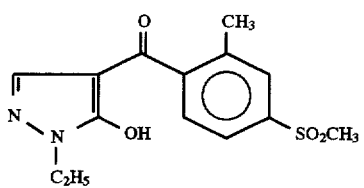

(B)

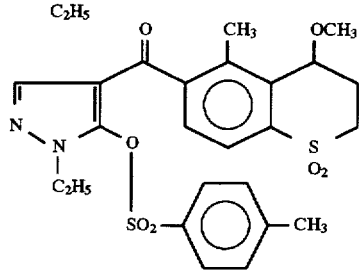

(C)

(2) Biological test (Submergence soil treatment test)

A 1/15,500-are porcelain pot was filled with paddy field soil, and seeds of barnyardgrass and umbrella plant were sown in a surface layer of the soil, and paddy rice at the two-leaf stage was transplanted.

Then, a diluted solution of a predetermined amount of the herbicide prepared in the above (1) was uniformly sprayed onto the water surface at the time of germination of the weeds, and then the pot was allowed to stand in a greenhouse while water was properly sprayed.

Twenty days after the treatment with the herbicide solution, the herbicidal efficacy and phytotoxicity to paddy rice were inspected, and Tables 26 to 29 show the results. The dosage of the herbicide is shown as an amount of the effective ingredient per 10 ares. Further, air-dried weights were measured, and the phytotoxicity to paddy rice and the herbicidal efficacy were shown as follows.

The ratio of remaining plant weight to non-treated was determined as the ratio of remaining plant weight to non-treated=(remaining plant weight in treated plot/remaining plant weight in non-treated plot)×100.

| Herbicidal efficacy | Ratio of remaining plant weight to non-treated (%) |
|---|---|
| 0 | 81–100 |
| 1 | 61–80 |
| 2 | 41–60 |
| 3 | 21–40 |
| 4 | 1–20 |
| 5 | 0 |
| Phytotoxicity to paddy rice | |
| 0 | 100 |
| 1 | 95–99 |
| 2 | 90–94 |
| 3 | 80–89 |
| 4 | 0–79 |

TABLE 26

| herbicide Example No. | Active ingredient of herbicide | Dosage of active ingredient (g/10 are) | Herbicide efficacy barnyard glass | Herbicide efficacy umbrella plant | phytotoxicity to paddy rice |
|---|---|---|---|---|---|
| 1 | Comp. No. 1 | 3 | 5 | 5 | 0 |
| 2 | Comp. No. 1 | 1 | 5 | 5 | 0 |
| 3 | Comp. No. 2 | 3 | 5 | 5 | 0 |
| 4 | Comp. No. 2 | 1 | 5 | 5 | 0 |
| 5 | Comp. No. 3 | 3 | 5 | 5 | 0 |
| 6 | Comp. No. 3 | 1 | 5 | 5 | 0 |
| 10 | Comp. No. 4 | 3 | 5 | 5 | 0 |
| 11 | Comp. No. 4 | 1 | 5 | 5 | 0 |
| 12 | Comp. No. 5 | 3 | 5 | 5 | 0 |
| 13 | Comp. No. 5 | 1 | 5 | 5 | 0 |
| 14 | Comp. No. 6 | 3 | 5 | 5 | 0 |
| 15 | Comp. No. 6 | 1 | 5 | 5 | 0 |
| 16 | Comp. No. 7 | 3 | 5 | 5 | 0 |
| 17 | Comp. No. 7 | 1 | 5 | 5 | 0 |
| 18 | Comp. No. 8 | 3 | 5 | 5 | 0 |
| 19 | Comp. No. 8 | 1 | 5 | 5 | 0 |

TABLE 27

| herbicide Example No. | Active ingredient of herbicide | Dosage of active ingredient (g/10 are) | Herbicide efficacy barnyard glass | Herbicide efficacy umbrella plant | phytotoxicity to paddy rice |
|---|---|---|---|---|---|
| 20 | Comp. No. 9 | 3 | 5 | 5 | 0 |
| 21 | Comp. No. 9 | 1 | 5 | 5 | 0 |
| 22 | Comp. No. 10 | 3 | 5 | 5 | 0 |
| 23 | Comp. No. 10 | 1 | 5 | 5 | 0 |
| 24 | Comp. No. 11 | 3 | 5 | 5 | 0 |
| 25 | Comp. No. 11 | 1 | 5 | 5 | 0 |
| 26 | Comp. No. 12 | 3 | 5 | 5 | 0 |
| 27 | Comp. No. 12 | 1 | 5 | 5 | 0 |
| 28 | Comp. No. 13 | 3 | 5 | 5 | 0 |
| 29 | Comp. No. 13 | 1 | 3 | 4 | 0 |
| 30 | Comp. No. 14 | 3 | 5 | 5 | 0 |
| 31 | Comp. No. 14 | 1 | 4 | 3 | 0 |
| 32 | Comp. No. 15 | 3 | 5 | 5 | 0 |
| 33 | Comp. No. 15 | 1 | 5 | 3 | 0 |
| 34 | Comp. No. 16 | 3 | 5 | 5 | 0 |
| 35 | Comp. No. 16 | 1 | 5 | 5 | 0 |

TABLE 28

| herbicide Example No. | Active ingredient of herbicide | Dosage of active ingredient (g/10 are) | Herbicide efficacy barnyard glass | Herbicide efficacy umbrella plant | phytotoxicity to paddy rice |
|---|---|---|---|---|---|
| 36 | Comp. No. 17 | 3 | 5 | 5 | 0 |
| 37 | Comp. No. 17 | 1 | 2 | 2 | 0 |
| 38 | Comp. No. 18 | 3 | 5 | 5 | 0 |
| 39 | Comp. No. 18 | 1 | 5 | 3 | 0 |
| 40 | Comp. No. 19 | 3 | 5 | 5 | 0 |
| 41 | Comp. No. 19 | 1 | 5 | 3 | 0 |
| 42 | Comp. No. 20 | 3 | 5 | 5 | 0 |
| 43 | Comp. No. 20 | 1 | 4 | 5 | 0 |
| 44 | Comp. No. 21 | 3 | 5 | 5 | 0 |
| 45 | Comp. No. 21 | 1 | 5 | 5 | 0 |
| 46 | Comp. No. 22 | 3 | 5 | 5 | 0 |
| 47 | Comp. No. 22 | 1 | 5 | 5 | 0 |

TABLE 28-continued

| herbicide Example No. | Active ingredient of herbicide | Dosage of active ingredient (g/10 are) | Herbicide efficacy | | phyto- toxicity to paddy rice |
|---|---|---|---|---|---|
| | | | barnyard glass | umbrella plant | |
| 48 | Comp. No. 23 | 3 | 5 | 5 | 0 |
| 49 | Comp. No. 23 | 1 | 5 | 5 | 0 |
| 50 | Comp. No. 24 | 3 | 5 | 5 | 0 |
| 51 | Comp. No. 24 | 1 | 4 | 5 | 0 |

TABLE 29

| herbicide Example No. | Active ingredient of herbicide | Dosage of active ingredient (g/10 are) | Herbicide efficacy | | phyto- toxicity to paddy rice |
|---|---|---|---|---|---|
| | | | barnyard glass | umbrella plant | |
| 52 | Comp. No. 25 | 3 | 5 | 5 | 0 |
| 53 | Comp. No. 25 | 1 | 2 | 3 | 0 |
| 54 | Comp. No. 26 | 3 | 5 | 5 | 0 |
| 55 | Comp. No. 26 | 1 | 5 | 5 | 0 |
| 56 | Comp. No. 27 | 3 | 5 | 5 | 0 |
| 57 | Comp. No. 27 | 1 | 5 | 5 | 0 |
| 58 | Comp. No. 28 | 3 | 5 | 5 | 0 |
| 59 | Comp. No. 28 | 1 | 5 | 3 | 0 |
| 60 | Comp. No. 29 | 3 | 5 | 5 | 0 |
| 61 | Comp. No. 29 | 1 | 5 | 5 | 0 |
| 87 | Comp. No. 30 | 1 | 4 | 5 | 0 |
| 88 | Comp. No. 31 | 1 | 5 | 5 | 0 |
| 89 | Comp. No. 32 | 1 | 5 | 5 | 0 |
| 90 | Comp. No. 33 | 1 | 5 | 5 | 0 |
| Comp. Ex. 1 | Comp. A | 3 | 4 | 4 | 4 |
| Comp. Ex. 2 | Comp. A | 1 | 1 | 0 | 0 |
| Comp. Ex. 3 | Comp. C | 3 | 5 | 5 | 4 |
| Comp. Ex. 4 | Comp. C | 1 | 2 | 3 | 0 |

(3) Biological test (Soil treatment test on upland soil)

Seeds of weeds such as large crabgrass, barnyardgrass, green foxtail cocklebur, velvetleaf and slender amaranth and seeds of corn were sown in 1/5,000-are Wagner pots filled with upland soil, and covered with upland soil. Then, a predetermined amount of the herbicide prepared in the above (1) was suspended in water and uniformly sprayed onto the soil surface. Thereafter, the seeds were grown in a greenhouse, and 20 days after the treatment, the herbicide was determined for herbicidal efficacy and phytotoxicity to corn. Tables 30 and 31 shows the results.

The dosage of the herbicide is shown as an amount of the effective ingredient per hectare. Further, air-dried weights were measured, and the phytotoxicity to corn and the herbicidal efficacy were shown as follows.

The ratio of remaining plant weight to non-treated was determined as the ratio of remaining plant weight to non-treated=(remaining plant weight in treated plot/remaining plant weight in non-treated plot)×100.

| | Ratio of remaining plant weight to non-treated (%) |
|---|---|
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity to corn | |
| 0 | 100 |
| 1 | 95–99 |
| 2 | 90–94 |
| 3 | 80–89 |
| 4 | 0–79 |

TABLE 30

| herbicide Example No. | Active ingredient of herbicide | Dosage of active ingredient (g/hectare) | Herbicide efficacy | | | | | | phytotoxicity to corn |
|---|---|---|---|---|---|---|---|---|---|
| | | | large crabgrass | barnyard grass | green foxtail | cockle- bur | velvet- leaf | slender amaranth | |
| 7 | Comp. No. 1 | 100 | 5 | 5 | 5 | 5 | 5 | 5 | 0 |
| 8 | Comp. No. 2 | 100 | 5 | 5 | 5 | 5 | 5 | 5 | 0 |
| 9 | Comp. No. 3 | 100 | 5 | 5 | 5 | 5 | 5 | 5 | 0 |
| 62 | Comp. No. 4 | 100 | 5 | 5 | 5 | 5 | 5 | 5 | 0 |
| 63 | Comp. No. 5 | 100 | 5 | 5 | 4 | 5 | 5 | 5 | 0 |
| 64 | Comp. No. 6 | 100 | 5 | 5 | 5 | 5 | 5 | 5 | 0 |
| 65 | Comp. No. 7 | 100 | 5 | 5 | 5 | 5 | 5 | 5 | 0 |
| 66 | Comp. No. 8 | 100 | 5 | 5 | 5 | 5 | 5 | 5 | 0 |
| 67 | Comp. No. 9 | 100 | 4 | 3 | 5 | 5 | 5 | 5 | 0 |
| 68 | Comp. No. 10 | 100 | 5 | 5 | 5 | 5 | 5 | 5 | 0 |
| 69 | Comp. No. 11 | 100 | 5 | 5 | 5 | 5 | 5 | 5 | 0 |
| 70 | Comp. No. 12 | 100 | 5 | 5 | 5 | 5 | 5 | 5 | 0 |
| 71 | Comp. No. 13 | 100 | 5 | 5 | 5 | 5 | 5 | 5 | 0 |
| 72 | Comp. No. 14 | 100 | 5 | 5 | 5 | 5 | 5 | 5 | 0 |
| 73 | Comp. No. 15 | 100 | 4 | 4 | 3 | 5 | 5 | 5 | 0 |
| 74 | Comp. No. 16 | 100 | 5 | 5 | 5 | 5 | 5 | 5 | 0 |

TABLE 31

| herbicide Example No. | Active ingredient of herbicide | Dosage of active ingredient (g/hectare) | Herbicide efficacy | | | | | | phytotoxicity to corn |
|---|---|---|---|---|---|---|---|---|---|
| | | | large crabgrass | barnyard grass | green foxtail | cockle-bur | velvet-leaf | slender amaranth | |
| 75 | Comp. No. 17 | 100 | 5 | 5 | 4 | 5 | 5 | 5 | 0 |
| 76 | Comp. No. 18 | 100 | 5 | 5 | 5 | 5 | 5 | 5 | 0 |
| 77 | Comp. No. 19 | 100 | 5 | 5 | 5 | 5 | 5 | 5 | 0 |
| 78 | Comp. No. 20 | 100 | 5 | 5 | 5 | 5 | 5 | 5 | 0 |
| 79 | Comp. No. 21 | 100 | 5 | 5 | 5 | 5 | 5 | 5 | 0 |
| 80 | Comp. No. 22 | 100 | 5 | 5 | 5 | 5 | 5 | 5 | 0 |
| 81 | Comp. No. 23 | 100 | 5 | 5 | 5 | 5 | 5 | 5 | 0 |
| 82 | Comp. No. 24 | 100 | 5 | 5 | 5 | 5 | 5 | 5 | 0 |
| 83 | Comp. No. 25 | 100 | 5 | 5 | 5 | 5 | 5 | 5 | 0 |
| 84 | Comp. No. 26 | 100 | 5 | 5 | 5 | 5 | 5 | 5 | 0 |
| 85 | Comp. No. 27 | 100 | 3 | 3 | 1 | 5 | 5 | 5 | 0 |
| 86 | Comp. No. 28 | 100 | 5 | 5 | 5 | 5 | 5 | 5 | 0 |
| 87 | Comp. No. 29 | 100 | 5 | 5 | 5 | 5 | 2 | 5 | 0 |
| 91 | Comp. No. 30 | 100 | 5 | 5 | 4 | 5 | 4 | 5 | 0 |
| 92 | Comp. No. 31 | 100 | 5 | 5 | 3 | 5 | 5 | 5 | 0 |
| 93 | Comp. No. 32 | 100 | 4 | 5 | 1 | 2 | 5 | 5 | 0 |
| 94 | Comp. No. 33 | 100 | 5 | 5 | 3 | 5 | 4 | 5 | 0 |
| Comp. Ex. 5 | Comp. A | 100 | 1 | 2 | 4 | 1 | 5 | 3 | 0 |
| Comp. Ex. 6 | Comp. B | 300 | 1 | 1 | 1 | 2 | 0 | 0 | 0 |

Tables 26 to 31 clearly show that the herbicides containing pyrazole derivatives of the formula (I), provided by the present invention, can control a wide range of paddy field and upland field weeds at low dosages without causing phytotoxicity to paddy rice and corn.

(11) Preparation of herbicide containing pyrazole compound of the formula (XI)

97 Parts by weight of talc (trade name: Zeaklite) as a carrier, 1.5 parts by weight of alkylarylsulfonic acid (trade name: Neoplex, supplied by Kao-Atlas K. K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier and 10 parts by weight of one of compounds of formula (XI) of the present invention obtained in the above Preparation Examples (or 10 parts by weight of the following Compound (C) for Herbicide Comparative Example) were uniformly pulverized and mixed to obtain a herbicide.

Compound (C) used in Herbicide Comparative Example is Compound No. 66 in PCT/JP93/00274 (WO93/18031), and has the following structure.

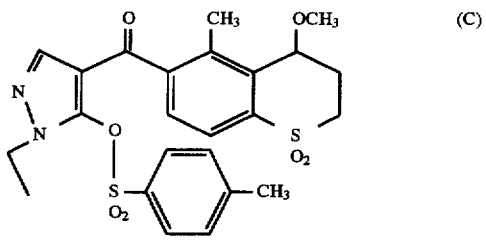

(12) Biological test (Submergence soil treatment test) A 1/15,500-are porcelain pot was filled with paddy field soil, and seeds of barnyardgrass and umbrella plant were sown in a surface layer of the soil, and paddy rice at the 2.5-leaf stage was transplanted.

Then, a diluted solution of a predetermined amount of the herbicide prepared in the above (11) was uniformly sprayed onto the water surface at the time of germination of the weeds, and then the pot was allowed to stand in a greenhouse while water was properly sprayed.

Twenty days after the treatment with the herbicide solution, the herbicidal efficacy and phytotoxicity to paddy rice were inspected, and Table 32 shows the results. The dosage of the herbicide is shown as an amount of the effective ingredient per 10 ares. Further, air-dried weights were measured, and the phytotoxicity to paddy rice and the herbicidal efficacy were shown as follows.

| | Ratio of remaining plant weight to non-treated (%) |
|---|---|
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity to paddy rice | |
| 0 | 100 |
| 1 | 95–99 |
| 2 | 90–94 |
| 3 | 80–89 |
| 4 | 0–79 |

The ratio of remaining plant weight to non-treated was determined as the ratio of remaining plant weight to non-treated=(remaining plant weight in treated plot/remaining plant weight in non-treated plot)×100.

TABLE 32

| herbicide Example No. | Comp. No. | Dosage of active ingredient (g/10a) | Herbicide efficacy barnyard glass | Herbicide efficacy umbrella plant | phytotoxicity to paddy rice |
|---|---|---|---|---|---|
| 101 | 52 | 1 | 5 | 5 | 0 |
| 102 | 53 | 3 | 5 | 5 | 0 |
| 103 | 54 | 3 | 5 | 5 | 0 |
| 104 | 55 | 3 | 5 | 5 | 0 |
| 105 | 56 | 3 | 5 | 5 | 0 |
| 106 | 57 | 3 | 5 | 5 | 0 |
| 107 | 58 | 1 | 5 | 5 | 0 |
| 108 | 59 | 3 | 5 | 5 | 0 |
| Comp. Ex. 11 | (C) | 3 1 | 5 2 | 5 3 | 4 0 |

Table 32 clearly shows that the compound of the present invention can completely control barnyardgrass and umbrella plant at a low dosage without causing phytotoxicity to paddy rice.

For reference purpose, Preparation Example of the production of a starting material for the production of the compound of the formula (I) of the present invention will be described below.

[Preparation Example of Starting Material]

Figure 4:
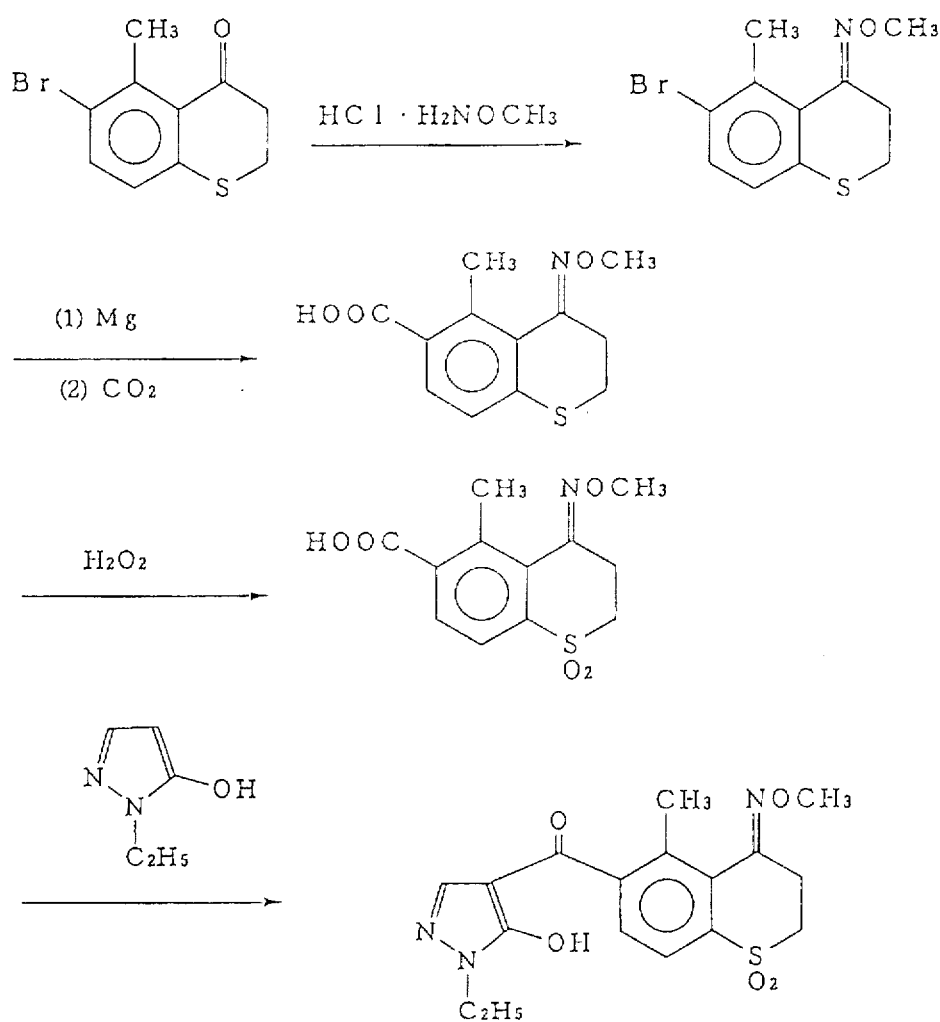
FIG. 4 shows the step of producing 4-methoxyimino-5-methyl-6-(1-ethyl-5-hydroxypyrazole-4-carbonylthiochroman-1,1-dioxide which is one of starting materials.

Preparation of 4-methoxyimino-5-methyl-6(1-ethyl-5-hydroxypyrazol-4-yl)carbonylthiochroman-1,1-dioxide (see FIG. 4)

(1) 3.0 Grams (12 mmol) of 5-methyl-6-bromothiochroman-4-one and 1.9 g (23 mmol) of O-methylhydroxylamine hydrochloride were refluxed in a solvent mixture of 10 ml of ethanol and 10 ml of pyridine under heat for 30 minutes. The solvents were distilled off under reduced pressure, 50 ml of 5% hydrochloric acid was added, and a formed solid was recovered by filtration, washed with water and then dried to give 3.2 g (yield 93%) of 4-methoxyimino-5-methyl-6-bromothiochroman.

(2) 1.1 Grams (46 mmol) of magnesium was dispersed in 10 ml of THF, and 2.2 g (20 mmol) of ethyl bromide was dropwise added under nitrogen current. The mixture was allowed to react for 10 minutes, and then a THF solution of 2.9 g (10 mmol) of the 4-methoxyimino-5-methyl-6-bromothiochroman obtained in the above (1) was gradually added at room temperature. The mixture was refluxed for 3 hours and then cooled to room temperature, and carbon dioxide gas was bubbled in for 1 hour. To the reaction mixture was added 5% hydrochloric acid, and the mixture was extracted with ether. An ether layer was extracted with a 5% potassium carbonate aqueous solution, and an aqueous layer was neutralized with concentrated hydrochloric acid. The neutralization product was extracted with ethyl acetate, and the extract was washed with a saturated sodium chloride aqueous solution. The washed extract was dried over sodium sulfate, and then the solvent was distilled off to give 1.6 g (yield 63%) of 4-methoxyimino-5-methylthiochroman-6-carboxylic acid.

(3) 1.0 Gram (4.0 mmol) of the 4-methoxyimino-5-methylthiochroman-6-carboxylic acid obtained in the above (2) was reacted with 1.3 g (12 mmol) of a 30% hydrogen peroxide aqueous solution in 5 ml of acetic acid at 100° C. for 1 hour. Ethyl acetate was added to the reaction product, and the mixture was washed with a saturated sodium chloride aqueous solution and then dried over sodium sulfate. The solvent was distilled off to give 1.1 g (yield 97%) of 4-methoxyimino-5-methylthiochroman-6-carboxylic acid-1,1-dioxide.

(4) 0.9 Gram (3.2 mmol) of the 4-methoxyimino-5-methylthiochroman-6-carboxylic acid-1,1-dioxide and 0.44 g (3.9 mmol) of 1-ethyl-5-hydroxypyrazol were dissolved in 5 ml of t-amyl alcohol, and 0.81 g (3.9 mmol) of DCC (dicyclohexyl-carbodiimide) was added at room temperature. The mixture was stirred at room temperature for 2 hours, then, 0.74 g (5.4 mmol) of potassium carbonate was added, and the mixture was allowed to react at 90° C. for 8 hours. After the reaction, the solvent was distilled off, ethyl acetate was added, and the mixture was extracted with a 5% potassium carbonate aqueous solution. An aqueous layer was neutralized with concentrated hydrochloric acid, and extracted with ethyl acetate. The extract was washed with a saturated sodium hydroxide aqueous solution, dried over sodium sulfate and concentrated to give 0.88 g (yield 72%) of 4-methoxyimino-5-methyl-6-(1-ethyl-5-hydroxypyrazol-4-yl) carbonylthiochroman-1,1-dioxide.

The result of the measurement thereof by NMR (ppm, solvent: deutero DMSO, internal standard; tetramethylsilane) was as follows.

1.28 (3H, t) 2.58 (3H, s) 3.1–3.7 (4H, m)
4.02 (3H, s) 3.0–4.2 (2H, m)
7.5–8.0 (2h, m) 7.82 (1H, s)

As explained above, the present invention provides pyrazol derivatives and herbicides containing them as an active ingredient, which are free of phytotoxicity to paddy rice and corn and can control a wide range of paddy field and upland field weeds at a low dosage.

We claim:

1. A pyrazole compound of the formula (I),

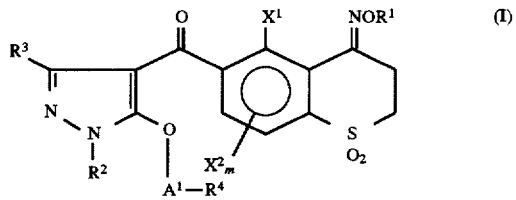

wherein $R^1$ is a $C_1$–$C_6$ alkyl group, each of $R^2$, $X^1$ and $X^2$ is independently a $C_1$–$C_4$ alkyl group, $R^3$ is hydrogen or a $C_1$–$C_4$ alkyl group, m is 0 or 1, $R^4$ is a $C_1$–$C_4$ alkyl group or a group of the formula,

wherein Y is a halogen atom, nitro, a $C_1$–$C_4$ alkoxy group or a $C_1$–$C_4$ alkyl group, and n is an integer of 0 to 3, $A^1$ is

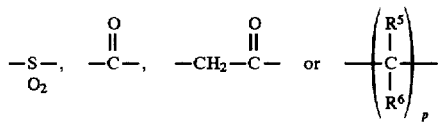

in which each of $R^5$ and $R^6$ is independently hydrogen or a $C_1$–$C_4$ alkyl group and p is 0 or an integer of 1 to 4.

2. The pyrazole compound of claim 1, wherein $R^1$ is a $C_1$–$C_4$ alkyl group.

3. The pyrazole compound of claim 2, wherein $R^1$ is methyl or ethyl.

4. The pyrazole compound of claim 1, wherein each of $R^2$, $X^1$ and $X^2$ is independently methyl or ethyl.

5. The pyrazole compound of claim 1, wherein $R^3$ is hydrogen or methyl.

6. The pyrazole compound of claim 1, wherein, when m is 1, $X^2$ is substituted on the 8-position of a thiochroman ring.

7. The pyrazole compound of claim 1, wherein $R^4$ is a $C_1$–$C_4$ alkyl group.

8. The pyrazole compound of claim 1, wherein $R^4$ is the group of the formula,

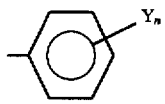

in which Y is chlorine, fluorine, nitro, methyl or methoxy.

9. The pyrazole compound of claim 1, wherein $A^1$ is the formula of

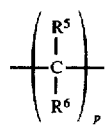

and is —$CH_2$—.

10. A herbicide containing, as an active ingredient, the pyrazole compound as recited in claim 1.

11. The herbicide of claim 10, wherein the herbicide further contains at least one substance selected from the group consisting of a pesticide, a fungicide, a plant growth regulator and a fertilizer.

* * * * *